US011559653B2

(12) United States Patent
Osborne et al.

(10) Patent No.: US 11,559,653 B2
(45) Date of Patent: *Jan. 24, 2023

(54) RESPIRATORY HUMIDIFICATION SYSTEM

(71) Applicant: FISHER & PAYKEL HEALTHCARE LIMITED, Auckland (NZ)

(72) Inventors: Hamish Adrian Osborne, Auckland (NZ); Jonathan David Harwood, Auckland (NZ); Natalie May Robertson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 290 days.

This patent is subject to a terminal disclaimer.

(21) Appl. No.: 16/571,671

(22) Filed: Sep. 16, 2019

(65) Prior Publication Data

US 2020/0101253 A1    Apr. 2, 2020

Related U.S. Application Data

(63) Continuation of application No. 15/115,751, filed as application No. PCT/NZ2015/050011 on Feb. 9, 2015, now Pat. No. 10,449,319.

(Continued)

(51) Int. Cl.
*A61M 16/08* (2006.01)
*A61M 16/16* (2006.01)
(Continued)

(52) U.S. Cl.
CPC ...... *A61M 16/0808* (2013.01); *A61M 16/024* (2017.08); *A61M 16/0816* (2013.01);
(Continued)

(58) Field of Classification Search
CPC .. A61M 16/00; A61M 16/0057; A61M 16/08; A61M 16/0808; A61M 16/0816;
(Continued)

(56) References Cited

U.S. PATENT DOCUMENTS 1,085,833 A    2/1914  Wilson
1,154,259 A    9/1915  Light
(Continued)

FOREIGN PATENT DOCUMENTS

AU    667538    3/1996
AU    726022    10/2000
(Continued)

OTHER PUBLICATIONS

ISR for Inernational App No. PCT/NZ2015/050011; dated Mar. 19, 2015, 4 pages.

*Primary Examiner* — Joseph D. Boecker
(74) *Attorney, Agent, or Firm* — Knobbe Martens Olson & Bear, LLP

(57) ABSTRACT

A system provides warm, humidified pas to a patient via a patient interface. Horizontal connections can be used between the humidification chamber and conduit. To reduce the likelihood of condensate flowing back to the humidification chamber, or dead space or gases recirculation regions occurring within the gases flow path, a raised portion is positioned inside of the flow path to improve flow characteristics and to provide a barrier for condensate back flow. The raised portion also reduces the amount of condensate that is formed in the system and provides better flow characteristics for sensing purposes.

18 Claims, 18 Drawing Sheets

Related U.S. Application Data

(60) Provisional application No. 61/937,017, filed on Feb. 7, 2014.

(51) Int. Cl.
*A61M 16/00* (2006.01)
*A61M 16/10* (2006.01)
*F15D 1/06* (2006.01)
F24F 13/08 (2006.01)

(52) U.S. Cl.
CPC ...... *A61M 16/0875* (2013.01); *A61M 16/109* (2014.02); *A61M 16/1095* (2014.02); *A61M 16/16* (2013.01); A61M 2205/3368 (2013.01); A61M 2205/50 (2013.01); *F15D 1/06* (2013.01); *F24F 13/081* (2013.01)

(58) Field of Classification Search
CPC .......... A61M 16/0825; A61M 16/0833; A61M 16/0875; A61M 16/0883; A61M 16/1085; A61M 16/109; A61M 16/1095; A61M 11/041; A61M 11/042; A61M 2205/3368; F24F 2006/008; F24F 6/12; F24F 6/14; F24F 13/081; Y10S 128/909; Y10S 128/911; Y10S 128/912; Y10S 128/913; F15D 1/02; F15D 1/04; F15D 1/06
USPC .......................................................... 138/39
See application file for complete search history.

(56) References Cited

U.S. PATENT DOCUMENTS

| | | |
|---|---|---|
| 2,073,335 A | 3/1937 | Connell |
| 2,510,125 A | 6/1950 | Meakin |
| 2,516,864 A | 8/1950 | Gilmore et al. |
| 2,745,074 A | 1/1951 | Darling |
| 2,590,797 A | 3/1952 | Siciliano |
| 2,621,875 A | 12/1952 | Darling |
| 2,634,311 A | 4/1953 | Darling |
| 3,117,596 A | 1/1964 | Kahn |
| 3,163,707 A | 12/1964 | Darling |
| 3,283,580 A | 11/1966 | Jacob et al. |
| 3,394,954 A | 7/1968 | Sarns |
| 3,404,684 A | 10/1968 | Brewer et al. |
| 3,485,237 A | 12/1969 | Bedford |
| 3,495,628 A | 2/1970 | Boender |
| 3,582,094 A | 6/1971 | Whittaker |
| 3,588,859 A | 6/1971 | Petree |
| 3,623,511 A | 11/1971 | Levin |
| 3,638,926 A | 2/1972 | Melville et al. |
| 3,659,604 A | 5/1972 | Melville et al. |
| 3,703,892 A | 11/1972 | Meyers |
| 3,777,298 A | 12/1973 | Newman |
| 3,806,102 A | 4/1974 | Valenta et al. |
| 3,903,742 A | 9/1975 | Colton |
| 3,945,378 A | 3/1976 | Paluch |
| 3,954,920 A | 5/1976 | Heath |
| 3,987,133 A | 10/1976 | Andra |
| 3,990,727 A | 11/1976 | Gallagher |
| 4,010,748 A | 3/1977 | Dobritz |
| 4,028,444 A | 6/1977 | Brown |
| 4,038,519 A | 7/1977 | Foucras |
| 4,060,576 A | 11/1977 | Grant |
| 4,098,853 A | 7/1978 | Brown et al. |
| 4,111,197 A | 9/1978 | Warncke et al. |
| 4,139,762 A | 2/1979 | Pohrer et al. |
| 4,152,379 A | 5/1979 | Suhr |
| 4,160,466 A | 7/1979 | Jousson |
| 4,172,709 A | 10/1979 | Kippel et al. |
| 4,183,248 A | 1/1980 | West |
| 4,192,836 A | 3/1980 | Bartscher |
| 4,301,200 A | 11/1981 | Langenfeld et al. |
| 4,333,451 A | 6/1982 | Paluch |
| 4,417,574 A | 11/1983 | Taloon et al. |
| 4,428,403 A | 1/1984 | Lee |
| 4,463,593 A | 8/1984 | Parker |
| 4,473,923 A | 10/1984 | Neroni et al. |
| 4,529,867 A | 7/1985 | Velnosky et al. |
| 4,531,551 A | 7/1985 | Eichelberger et al. |
| 4,533,115 A | 8/1985 | Lissau |
| 4,545,290 A | 10/1985 | Lieberman |
| 4,558,708 A | 12/1985 | Labuda et al. |
| 4,564,748 A | 1/1986 | Gupton |
| 4,588,425 A | 5/1986 | Usry et al. |
| 4,599,895 A | 7/1986 | Wiseman |
| 4,621,632 A | 11/1986 | Bartels et al. |
| 4,676,237 A | 6/1987 | Wood et al. |
| 4,686,354 A | 8/1987 | Makin |
| 4,708,831 A | 11/1987 | Elsworth et al. |
| 4,714,078 A | 12/1987 | Paluch |
| 4,753,758 A | 6/1988 | Miller |
| 4,774,032 A | 9/1988 | Coates et al. |
| 4,809,698 A | 3/1989 | Kogo |
| 4,813,280 A | 3/1989 | Miller, Jr. et al. |
| 4,830,515 A | 5/1989 | Cortes |
| 4,844,512 A | 7/1989 | Gahwiler |
| 4,942,877 A | 7/1990 | Sakai et al. |
| 4,944,310 A | 7/1990 | Sullivan |
| 4,967,744 A | 11/1990 | Chua |
| 5,017,875 A | 5/1991 | Hori |
| 5,027,811 A | 7/1991 | Tuxill |
| 5,031,612 A | 7/1991 | Clementi |
| 5,038,773 A | 8/1991 | Norlien |
| 5,054,819 A | 10/1991 | Grunwald |
| 5,058,588 A | 10/1991 | Kaestle |
| 5,060,506 A | 10/1991 | Douglas |
| 5,062,145 A | 10/1991 | Zwaan |
| 5,117,819 A | 6/1992 | Servidio et al. |
| 5,127,442 A | 7/1992 | Blomqvist |
| 5,134,996 A | 8/1992 | Bell |
| 5,143,060 A | 9/1992 | Smith |
| 5,148,801 A | 9/1992 | Douwens et al. |
| 5,181,858 A | 1/1993 | Matz et al. |
| 5,209,225 A | 5/1993 | Glenn |
| 5,213,138 A | 5/1993 | Presz, Jr. |
| 5,213,376 A | 5/1993 | Szabo |
| 5,233,996 A | 8/1993 | Coleman et al. |
| 5,303,701 A | 4/1994 | Heins et al. |
| RE34,599 E | 5/1994 | Suszynski et al. |
| 5,342,126 A | 8/1994 | Heston |
| 5,357,948 A | 10/1994 | Eilentropp |
| 5,367,604 A | 11/1994 | Murray |
| 5,392,770 A | 2/1995 | Clawson et al. |
| 5,396,884 A | 3/1995 | Bagwell et al. |
| 5,454,061 A | 9/1995 | Carlson |
| 5,454,479 A | 10/1995 | Kraus |
| 5,483,616 A | 1/1996 | Chiu et al. |
| 5,484,223 A | 1/1996 | Saito |
| 5,488,447 A | 1/1996 | Patton |
| 5,495,872 A | 3/1996 | Gallagher et al. |
| 5,499,737 A | 3/1996 | Kraus |
| RE35,225 E | 4/1996 | Herweck et al. |
| 5,529,093 A | 6/1996 | Gallagher et al. |
| 5,537,996 A | 7/1996 | McPhee |
| 5,540,219 A | 7/1996 | Mechlenburg et al. |
| 5,548,879 A | 8/1996 | Wu |
| 5,551,883 A | 9/1996 | Davis |
| 5,558,084 A | 9/1996 | Daniell |
| 5,564,415 A | 10/1996 | Dobson et al. |
| 5,598,837 A | 2/1997 | Sirianne et al. |
| 5,600,752 A | 2/1997 | Lopatinsky |
| 5,630,806 A | 5/1997 | Inagaki et al. |
| 5,637,006 A | 6/1997 | Almeras |
| 5,640,951 A * | 6/1997 | Huddart ................ A61M 16/08 128/204.17 |
| 5,660,567 A | 8/1997 | Nierlich et al. |
| 5,667,306 A | 9/1997 | Montreuil |
| 5,720,293 A | 2/1998 | Nierlich et al. |
| 5,778,872 A | 7/1998 | Fukunaga et al. |
| 5,829,880 A | 11/1998 | Diedrich |
| 5,881,393 A | 3/1999 | Marchello |
| 5,906,201 A | 5/1999 | Nilson |
| 5,913,249 A | 6/1999 | Weckstrom |

(56) References Cited

U.S. PATENT DOCUMENTS

| | | |
|---|---|---|
| 5,943,473 A | 8/1999 | Levine |
| 5,975,591 A | 11/1999 | Guest |
| 5,979,247 A | 11/1999 | Kizawa |
| D419,522 S | 1/2000 | Kamagai |
| 6,024,694 A | 2/2000 | Godlberg |
| 6,039,696 A | 3/2000 | Bell |
| 6,050,260 A | 4/2000 | Daniell |
| 6,053,482 A | 4/2000 | Glenn et al. |
| 6,058,977 A | 5/2000 | Hotta |
| 6,078,729 A | 6/2000 | Kopel |
| 6,078,730 A | 6/2000 | Huddart et al. |
| 6,095,505 A | 8/2000 | Miller |
| 6,102,037 A | 8/2000 | Koch |
| 6,105,970 A | 8/2000 | Siegrist et al. |
| 6,126,610 A | 10/2000 | Rich et al. |
| 6,128,963 A | 10/2000 | Bromster |
| 6,138,674 A | 10/2000 | Gull et al. |
| 6,190,480 B1 | 2/2001 | Carlson |
| 6,196,980 B1 | 3/2001 | Akerfeldt et al. |
| 6,201,983 B1 | 3/2001 | Haumann et al. |
| 6,208,514 B1 | 3/2001 | Stark |
| 6,226,451 B1 | 5/2001 | Wong |
| 6,272,933 B1 | 8/2001 | Gradon et al. |
| 6,332,462 B1 | 12/2001 | Krohn |
| 6,347,646 B2 | 2/2002 | Fikui |
| 6,349,722 B1 | 2/2002 | Gradon et al. |
| 6,349,724 B1 | 2/2002 | Burton et al. |
| 6,360,741 B2 | 3/2002 | Truschel |
| 6,367,974 B1 | 4/2002 | Lin |
| 6,374,864 B1 | 4/2002 | Philip |
| 6,394,145 B1 | 5/2002 | Gessil |
| 6,397,841 B1 | 6/2002 | Kenyon et al. |
| 6,402,207 B1 | 6/2002 | Segal et al. |
| 6,435,180 B1 | 8/2002 | Hewson et al. |
| 6,467,477 B1 | 10/2002 | Frank et al. |
| 6,508,249 B2 | 1/2003 | Hoenig |
| 6,511,075 B1 | 1/2003 | Schmidt |
| 6,540,734 B1 | 4/2003 | Chiu |
| 6,551,143 B2 | 4/2003 | Tanaka et al. |
| 6,554,260 B1 | 4/2003 | Lipscombe et al. |
| 6,591,061 B2 | 7/2003 | Wang |
| 6,598,604 B1 | 7/2003 | Seakins |
| 6,600,727 B1 | 7/2003 | Mackay |
| 6,612,624 B1 | 9/2003 | Segal et al. |
| 6,623,352 B2 | 9/2003 | Illingworth |
| 6,631,718 B1 | 10/2003 | Lovell |
| 6,648,669 B1 | 11/2003 | Kim et al. |
| 6,655,207 B1 | 12/2003 | Speldrich et al. |
| 6,668,828 B1 | 12/2003 | Figley et al. |
| 6,685,491 B2 | 2/2004 | Gergek |
| 6,698,966 B2 | 3/2004 | Hilton et al. |
| 6,824,180 B2 | 11/2004 | Tomchak |
| 6,827,084 B2 | 12/2004 | Grubb, Jr. |
| 6,874,771 B2 | 4/2005 | Birdsell et al. |
| 6,895,803 B2 | 5/2005 | Seakins et al. |
| 6,915,705 B1 | 7/2005 | Truitt |
| 6,918,389 B2 | 7/2005 | Seakiins et al. |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardelius et al. |
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,316,768 B2 | 1/2008 | Aldridge et al. |
| 7,316,769 B2 | 1/2008 | Aldridge |
| 7,327,547 B1 | 2/2008 | Epstein |
| 7,327,949 B1 | 2/2008 | Cheng et al. |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,469,586 B2 | 12/2008 | Wild et al. |
| 7,478,635 B2 | 1/2009 | Wixey et al. |
| 7,525,663 B2 | 4/2009 | Kwok et al. |
| 7,607,360 B2 | 10/2009 | Todokoro et al. |
| 7,614,398 B2 | 11/2009 | Virr et al. |
| 7,637,288 B2 | 12/2009 | Kressierer/Huber et al. |
| 7,677,246 B2 | 3/2010 | Kepler et al. |
| 7,743,767 B2 | 6/2010 | Ging et al. |
| 7,766,050 B2 | 8/2010 | Patel |
| 7,794,426 B2 | 9/2010 | Briones et al. |
| 7,814,907 B2 | 10/2010 | Bremner et al. |
| 7,816,888 B2 | 10/2010 | Rejman et al. |
| D628,288 S | 11/2010 | Row et al. |
| 7,827,981 B2 | 11/2010 | Barnford |
| 7,870,857 B2 | 1/2011 | Dhuper et al. |
| 7,874,291 B2 | 1/2011 | Ging et al. |
| 7,900,528 B2 | 3/2011 | Vincent |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,206,337 B2 | 6/2012 | Blackhurst et al. |
| 8,221,530 B2 | 7/2012 | Peter et al. |
| 8,226,293 B2 | 7/2012 | Faries, Jr. |
| 8,240,306 B2 | 8/2012 | Cortez, Jr. et al. |
| 8,245,709 B2 | 8/2012 | Rossen et al. |
| 8,245,710 B2 | 8/2012 | Makinson et al. |
| 8,253,076 B2 | 8/2012 | Andel et al. |
| 8,267,084 B2 | 8/2012 | Kwok |
| 8,257,286 B2 | 9/2012 | Meyer et al. |
| 8,267,614 B2 | 9/2012 | Khoe |
| 8,282,427 B2 | 10/2012 | Yamazaki |
| 8,287,517 B2 | 10/2012 | Hanlon et al. |
| 8,316,848 B2 | 11/2012 | Kwok et al. |
| 8,333,194 B2 | 12/2012 | Hanlon et al. |
| 8,333,195 B2 | 12/2012 | Cortez, Jr. et al. |
| 8,333,199 B2 | 12/2012 | Landis et al. |
| 8,355,753 B2 | 1/2013 | Bochensko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,459,261 B2 | 6/2013 | Ricciardelli |
| 8,469,025 B2 | 6/2013 | Mayer et al. |
| 8,490,621 B2 | 7/2013 | Radomski et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,516,911 B2 | 8/2013 | Inoue |
| 8,522,782 B2 | 9/2013 | Lewis et al. |
| 8,528,552 B2 | 9/2013 | von Blumenthal |
| 8,544,465 B2 | 10/2013 | Smith et al. |
| 8,545,096 B2 | 10/2013 | Reiter |
| 8,550,072 B2 | 10/2013 | Thudor et al. |

(56) References Cited

U.S. PATENT DOCUMENTS

| | | | |
|---|---|---|---|
| 8,631,789 B2 | 1/2014 | Virr et al. | |
| 8,640,560 B2 | 2/2014 | Burke | |
| 8,640,696 B2 | 2/2014 | Pujol et al. | |
| 8,651,800 B2 | 2/2014 | Li | |
| 8,733,348 B2 | 5/2014 | Korneff et al. | |
| 8,733,349 B2 | 5/2014 | Bath et al. | |
| 8,756,990 B2 | 6/2014 | Speldrich | |
| 8,776,790 B2 | 7/2014 | Gentner et al. | |
| 8,783,252 B2 | 7/2014 | Pierro et al. | |
| 8,800,970 B2 | 8/2014 | Heine et al. | |
| 8,770,190 B2 | 9/2014 | McCarthy | |
| 8,844,388 B2 | 9/2014 | Burke | |
| 8,844,521 B2 | 9/2014 | McCarthy | |
| 8,851,071 B2 | 10/2014 | Kuo et al. | |
| 8,905,023 B2 | 12/2014 | Niland et al. | |
| 8,915,250 B2 | 12/2014 | Dugan et al. | |
| 8,931,481 B2 | 1/2015 | Jones et al. | |
| 8,939,147 B2 | 1/2015 | Henry et al. | |
| 8,985,105 B2 | 3/2015 | Burton et al. | |
| 8,997,740 B2 * | 4/2015 | Pujol | F24F 6/12 128/205.24 |
| 9,022,946 B2 | 5/2015 | Haque | |
| 9,039,277 B2 | 5/2015 | Le Bouquin et al. | |
| 9,067,036 B2 | 6/2015 | Kornell et al. | |
| 9,095,668 B2 | 8/2015 | Blackhurst et al. | |
| 9,119,933 B2 | 9/2015 | Bedford et al. | |
| 9,132,252 B2 | 9/2015 | Barlow et al. | |
| 9,162,035 B2 | 10/2015 | Kwok | |
| 9,186,477 B2 | 11/2015 | Hunt et al. | |
| 9,205,220 B2 | 12/2015 | Korneff et al. | |
| 9,212,673 B2 | 12/2015 | Korneff et al. | |
| 9,242,064 B2 | 1/2016 | Rustad et al. | |
| 9,254,368 B2 | 2/2016 | Blumental et al. | |
| 9,289,572 B2 | 3/2016 | Korneff et al. | |
| RE46,079 E | 7/2016 | Virr et al. | |
| 9,381,317 B2 | 7/2016 | Landis et al. | |
| 9,387,299 B2 | 7/2016 | Zwolinsky et al. | |
| 9,427,547 B2 | 8/2016 | Landis et al. | |
| 9,446,210 B2 | 9/2016 | Orr et al. | |
| 9,512,856 B2 | 12/2016 | Nibu | |
| 9,517,321 B2 | 12/2016 | Buechi et al. | |
| 9,545,493 B2 | 1/2017 | Mayer et al. | |
| 9,566,409 B2 | 2/2017 | Gründler et al. | |
| 9,572,949 B2 | 2/2017 | Vos et al. | |
| 9,572,951 B2 | 2/2017 | Barker et al. | |
| 9,586,019 B2 | 3/2017 | Heine et al. | |
| 9,642,979 B2 | 5/2017 | Korneff et al. | |
| RE46,571 E | 10/2017 | Virr et al. | |
| 9,838,759 B2 | 12/2017 | Kirmse et al. | |
| 9,861,778 B2 | 1/2018 | Roderick et al. | |
| 9,937,314 B2 | 4/2018 | Buechi et al. | |
| 9,937,316 B2 | 4/2018 | Buechi et al. | |
| 9,974,921 B2 | 5/2018 | Klenner et al. | |
| 9,987,455 B2 | 6/2018 | Stoks et al. | |
| 10,046,136 B2 | 8/2018 | Pujol | |
| 10,245,407 B2 | 4/2019 | Osborne et al. | |
| 10,449,319 B2 * | 10/2019 | Osborne | A61M 16/024 |
| 10,828,482 B2 | 11/2020 | Osborne et al. | |
| 10,974,015 B2 | 4/2021 | Stoks et al. | |
| 11,129,956 B2 | 9/2021 | Klenner et al. | |
| 11,324,911 B2 | 5/2022 | Osborne et al. | |
| 11,351,332 B2 | 6/2022 | Mcintyre et al. | |
| 2001/0017134 A1 | 8/2001 | Bahr | |
| 2001/0017880 A1 | 8/2001 | Beerwerth et al. | |
| 2001/0050080 A1 | 12/2001 | Seakins et al. | |
| 2002/0058436 A1 | 5/2002 | Saba | |
| 2002/0100320 A1 * | 8/2002 | Smith | A61M 16/1095 73/431 |
| 2002/0132511 A1 | 9/2002 | Groebe et al. | |
| 2002/0153011 A1 | 10/2002 | Tanhehco | |
| 2003/0066526 A1 | 4/2003 | Thurdor et al. | |
| 2003/0066530 A1 | 4/2003 | Shahbazpour et al. | |
| 2003/0107325 A1 | 6/2003 | Birkhead | |
| 2003/0127096 A1 | 7/2003 | McAuliffe | |
| 2003/0148664 A1 | 8/2003 | Cheng | |
| 2003/0154977 A1 | 8/2003 | White et al. | |
| 2003/0183294 A1 | 10/2003 | Carlson | |
| 2003/0200727 A1 | 10/2003 | Kim | |
| 2003/0236015 A1 | 12/2003 | Edirisuriya et al. | |
| 2004/0013162 A1 | 1/2004 | Beerwerth et al. | |
| 2004/0055597 A1 | 3/2004 | Virr et al. | |
| 2004/0074493 A1 | 4/2004 | Seakins et al. | |
| 2004/0079371 A1 | 4/2004 | Gray | |
| 2004/0087213 A1 | 5/2004 | Kao | |
| 2004/0099268 A1 | 5/2004 | Smith et al. | |
| 2004/0101026 A1 | 5/2004 | Nitta et al. | |
| 2004/0149284 A1 | 8/2004 | Smith et al. | |
| 2004/0168530 A1 | 9/2004 | Adolfs | |
| 2004/0182392 A1 | 9/2004 | Gerder et al. | |
| 2004/0221843 A1 | 11/2004 | Baecke | |
| 2004/0234254 A1 | 11/2004 | Czupich et al. | |
| 2004/0239001 A1 | 12/2004 | Edirisuriya et al. | |
| 2004/0244858 A1 | 12/2004 | Jeong | |
| 2005/0039809 A1 | 2/2005 | Speldrich | |
| 2005/0059957 A1 | 3/2005 | Campbell et al. | |
| 2005/0152733 A1 | 7/2005 | Patel | |
| 2006/0030191 A1 | 2/2006 | Tuin et al. | |
| 2006/0118113 A1 | 6/2006 | Bremner et al. | |
| 2006/0137445 A1 | 6/2006 | Smith et al. | |
| 2006/0150712 A1 | 7/2006 | Berstis et al. | |
| 2006/0165829 A1 | 7/2006 | Smith et al. | |
| 2006/0196510 A1 | 9/2006 | McDonald | |
| 2006/0237012 A1 | 10/2006 | Thurdor et al. | |
| 2006/0249160 A1 | 11/2006 | Scarberry | |
| 2006/0283450 A1 | 12/2006 | Shissler et al. | |
| 2007/0039374 A1 | 2/2007 | Borali | |
| 2007/0079982 A1 | 4/2007 | Laurent et al. | |
| 2007/0107737 A1 | 5/2007 | Landis et al. | |
| 2007/0110124 A1 | 5/2007 | Shiraki et al. | |
| 2007/0144519 A1 | 6/2007 | Henry et al. | |
| 2007/0157928 A1 | 7/2007 | Pujol et al. | |
| 2007/0169776 A1 | 7/2007 | Kepler et al. | |
| 2007/0175473 A1 | 8/2007 | Lewis et al. | |
| 2007/0193580 A1 | 8/2007 | Feldhahn et al. | |
| 2007/0248934 A1 | 10/2007 | Mosimann | |
| 2007/0272240 A1 | 11/2007 | Aylsworth et al. | |
| 2007/0284361 A1 | 12/2007 | Nadjafizadeh et al. | |
| 2008/0000474 A1 | 1/2008 | Jochle et al. | |
| 2008/0015257 A1 | 1/2008 | Grosskreutz et al. | |
| 2008/0027344 A1 | 1/2008 | Terry | |
| 2008/0028850 A1 | 2/2008 | Payton et al. | |
| 2008/0051674 A1 | 2/2008 | Davenport et al. | |
| 2008/0066741 A1 | 3/2008 | LeMahieu et al. | |
| 2008/0066751 A1 | 3/2008 | Polacsek | |
| 2008/0072900 A1 | 3/2008 | Kenyon et al. | |
| 2008/0105257 A1 | 5/2008 | Klasek et al. | |
| 2008/0142019 A1 | 6/2008 | Lewis et al. | |
| 2008/0196716 A1 | 8/2008 | Wachter | |
| 2008/0202512 A1 | 8/2008 | Kressierer | |
| 2008/0205481 A1 | 8/2008 | Faries | |
| 2008/0205979 A1 | 8/2008 | Gombert et al. | |
| 2008/0207028 A1 | 8/2008 | Schutz | |
| 2008/0251073 A1 | 10/2008 | Jassell et al. | |
| 2008/0264413 A1 | 10/2008 | Doherty et al. | |
| 2008/0302362 A1 | 12/2008 | Kwok | |
| 2008/0308169 A1 | 12/2008 | Nielsen | |
| 2009/0041080 A1 | 2/2009 | Koch | |
| 2009/0044808 A1 | 2/2009 | Guney et al. | |
| 2009/0050150 A1 | 2/2009 | Rossen et al. | |
| 2009/0056712 A1 | 3/2009 | Cortez, Jr. et al. | |
| 2009/0056713 A1 * | 3/2009 | Cortez, Jr. | A61M 16/1075 128/203.26 |
| 2009/0078259 A1 | 3/2009 | Kooji et al. | |
| 2009/0087259 A1 | 3/2009 | Kooji et al. | |
| 2009/0107493 A1 | 4/2009 | Liu et al. | |
| 2009/0107496 A1 | 4/2009 | McGhin et al. | |
| 2009/0107501 A1 | 4/2009 | Krieger | |
| 2009/0107981 A1 | 4/2009 | Andel et al. | |
| 2009/0110022 A1 | 4/2009 | Snyder et al. | |
| 2009/0110378 A1 | 4/2009 | Bradley et al. | |
| 2009/0174092 A1 | 7/2009 | Kwok et al. | |
| 2009/0180829 A1 | 7/2009 | Rejman et al. | |
| 2009/0223514 A1 | 9/2009 | Smith et al. | |
| 2009/0243226 A1 | 10/2009 | Liepold | |

(56) References Cited

U.S. PATENT DOCUMENTS

| | | |
|---|---|---|
| 2009/0247989 A1 | 10/2009 | Burke |
| 2009/0301482 A1 | 12/2009 | Burton et al. |
| 2009/0320840 A1 | 12/2009 | Klasek et al. |
| 2010/0015830 A1 | 1/2010 | Simeon et al. |
| 2010/0083965 A1 | 4/2010 | Virr et al. |
| 2010/0087749 A1 | 4/2010 | Tovey |
| 2010/0102799 A1 | 4/2010 | Schnidrig |
| 2010/0116272 A1 | 5/2010 | Row et al. |
| 2010/0147301 A1 | 6/2010 | Kwok |
| 2010/0154796 A1 | 6/2010 | Smith et al. |
| 2010/0204602 A1 | 8/2010 | Addington et al. |
| 2010/0242963 A1 | 9/2010 | Brieger et al. |
| 2010/0272507 A1 | 10/2010 | Khoe |
| 2010/0292601 A1 | 11/2010 | Dompeling et al. |
| 2011/0017212 A1 | 1/2011 | Kenyon et al. |
| 2011/0023874 A1 | 2/2011 | Bath et al. |
| 2011/0046433 A1 | 2/2011 | Khodak |
| 2011/0046494 A1 | 2/2011 | Balji et al. |
| 2011/0078109 A1 | 3/2011 | Mayer et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0180068 A1 | 7/2011 | Kenyon et al. |
| 2011/0186048 A1 | 8/2011 | Casse et al. |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0073573 A1 | 3/2012 | Thurdor et al. |
| 2012/0125333 A1 | 5/2012 | Bedford et al. |
| 2012/0125334 A1 | 5/2012 | Korneff et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0255758 A1 | 10/2012 | Lee |
| 2012/0266880 A1 | 10/2012 | Young |
| 2012/0283570 A1 | 11/2012 | Tegg |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0079667 A1 | 3/2013 | Berkcan et al. |
| 2013/0081619 A1 | 4/2013 | Seakins et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112201 A1 | 5/2013 | Graham et al. |
| 2013/0112202 A1 | 5/2013 | Fogelbrink |
| 2013/0152931 A1 | 6/2013 | Sims et al. |
| 2013/0174839 A1 | 7/2013 | Ging et al. |
| 2013/0199529 A1 | 8/2013 | Power et al. |
| 2013/0206140 A1 | 8/2013 | Kepler et al. |
| 2013/0237781 A1 | 9/2013 | Gyrn |
| 2013/0239960 A1 | 9/2013 | Bertinetti et al. |
| 2013/0239966 A1 | 9/2013 | Klasek et al. |
| 2013/0247905 A1 | 9/2013 | Miller et al. |
| 2013/0248044 A1* | 9/2013 | Shiga ............ F16L 9/00 138/156 |
| 2013/0252461 A1 | 9/2013 | Gross |
| 2013/0255677 A1 | 10/2013 | Varga |
| 2013/0333701 A1 | 12/2013 | Herron |
| 2013/0340752 A1 | 12/2013 | Landis et al. |
| 2014/0007872 A1 | 1/2014 | Grundler et al. |
| 2014/0020684 A1 | 1/2014 | Klasek et al. |
| 2014/0048065 A1 | 2/2014 | Haroutunian |
| 2014/0090649 A1 | 4/2014 | Groll et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0202462 A1 | 7/2014 | Stoks |
| 2014/0202463 A1 | 7/2014 | Ging et al. |
| 2014/0216446 A1 | 8/2014 | Wruck |
| 2014/0246021 A1 | 9/2014 | Buechi et al. |
| 2014/0251322 A1 | 9/2014 | Miller |
| 2014/0251331 A1 | 9/2014 | Korneff et al. |
| 2014/0283829 A1 | 9/2014 | Miller |
| 2014/0311489 A1 | 10/2014 | Heine et al. |
| 2014/0318536 A1 | 10/2014 | Landis et al. |
| 2014/0331786 A1 | 11/2014 | Romano |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0027204 A1 | 1/2015 | Stoks et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0096560 A1 | 4/2015 | Klenner et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015937 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0000968 A1 | 1/2017 | Harrington et al. |
| 2017/0095635 A1 | 4/2017 | Huby et al. |
| 2017/0136198 A1 | 5/2017 | Delangre et al. |
| 2017/0151411 A1 | 6/2017 | Osborne et al. |
| 2017/0161461 A1 | 6/2017 | Delangre et al. |
| 2017/0173293 A1 | 6/2017 | Osborne et al. |
| 2017/0197057 A1 | 7/2017 | Osborne et al. |
| 2017/0239432 A1 | 8/2017 | Delangre et al. |
| 2017/0326320 A1 | 11/2017 | Baigent et al. |
| 2018/0078730 A1 | 3/2018 | Bath et al. |
| 2018/0169361 A1 | 6/2018 | Dennis et al. |
| 2018/0214660 A1 | 8/2018 | Stoks et al. |
| 2018/0250491 A1 | 9/2018 | Row et al. |
| 2018/0296791 A1 | 10/2018 | Klenner et al. |
| 2019/0255278 A1 | 8/2019 | Osborne et al. |
| 2020/0061329 A1 | 2/2020 | Mcintyre et al. |
| 2021/0220601 A1 | 7/2021 | Stoks et al. |
| 2022/0031993 A1 | 2/2022 | Klenner et al. |

FOREIGN PATENT DOCUMENTS

| | | |
|---|---|---|
| AU | 2000071791 | 3/2001 |
| AU | 2001/020755 | 8/2001 |
| AU | 2001/028104 | 9/2001 |
| AU | 2002244571 | 9/2002 |
| AU | 2007317198 | 5/2008 |
| AU | 2010206053 | 2/2011 |
| AU | 2013201490 | 4/2013 |
| CA | 1202862 | 4/1986 |
| CA | 2464530 | 5/2003 |
| CA | 2495451 | 3/2004 |
| CA | 2535974 | 10/2011 |
| CA | 2393743 | 1/2012 |
| CA | 2852215 | 4/2013 |
| CN | 2243015 | 12/1996 |
| CN | 1598510 | 3/2005 |
| CN | 1688358 | 10/2005 |
| CN | 101541367 | 9/2009 |
| CN | 101666664 | 3/2010 |
| CN | 102844645 A | 12/2012 |
| CN | 201672170 | 12/2015 |
| DE | 3110903 | 9/1982 |
| DE | 3618614 | 12/1987 |

(56) References Cited

FOREIGN PATENT DOCUMENTS

| | | |
|---|---|---|
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 1020040307 47 | 1/2006 |
| DE | 20 2005 008 152.3 | 10/2006 |
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2004 021 759.7 | 10/2007 |
| DE | 20 2006 011 754.7 | 12/2007 |
| DE | 201 22 844.0 | 5/2008 |
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |
| DE | 20 2006 021 019.9 | 11/2011 |
| DE | 203 21 882.5 | 12/2011 |
| DE | 20 2004 021876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |
| EP | 0111248 | 6/1984 |
| EP | 0050984 | 12/1984 |
| EP | 0201985 | 11/1986 |
| EP | 0291921 | 11/1988 |
| EP | 0535952 | 4/1993 |
| EP | 0567158 | 10/1993 |
| EP | 0232864 | 5/1994 |
| EP | 0672430 | 9/1995 |
| EP | 0885623 | 12/1998 |
| EP | 1262208 | 12/2002 |
| EP | 1352670 | 10/2003 |
| EP | 1396277 | 3/2004 |
| EP | 1535722 | 6/2005 |
| EP | 1606000 | 12/2005 |
| EP | 1606001 | 12/2005 |
| EP | 1646910 | 4/2006 |
| EP | 1129743 | 5/2006 |
| EP | 1669098 | 6/2006 |
| EP | 1035887 | 7/2006 |
| EP | 1683066 | 7/2006 |
| EP | 1457223 B1 | 10/2006 |
| EP | 1741462 | 1/2007 |
| EP | 1837640 A2 | 9/2007 |
| EP | 1055431 | 11/2007 |
| EP | 1924311 | 5/2008 |
| EP | 1933914 | 6/2008 |
| EP | 1979030 | 10/2008 |
| EP | 2079505 | 7/2009 |
| EP | 2089086 | 8/2009 |
| EP | 2101851 | 9/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2340867 | 7/2011 |
| EP | 2355881 | 8/2011 |
| EP | 2133611 | 9/2011 |
| EP | 2415445 | 2/2012 |
| EP | 2471568 | 7/2012 |
| EP | 2498854 | 9/2012 |
| EP | 2281138 | 10/2012 |
| EP | 2514478 | 10/2012 |
| EP | 2575944 | 4/2013 |
| EP | 2613840 | 7/2013 |
| EP | 2629080 | 8/2013 |
| EP | 2640451 | 9/2013 |
| EP | 2651481 | 10/2013 |
| EP | 2654869 | 10/2013 |
| EP | 2667919 | 12/2013 |
| EP | 2522255 | 3/2014 |
| EP | 2703034 A2 | 3/2014 |
| EP | 2760516 | 8/2014 |
| EP | 2830695 | 2/2015 |
| EP | 2877224 | 6/2015 |
| EP | 2968829 | 1/2016 |
| EP | 3013402 | 5/2016 |
| EP | 1359962 | 8/2016 |
| EP | 3053623 | 8/2016 |
| EP | 3148418 | 4/2017 |
| EP | 3149696 | 4/2017 |
| EP | 3082920 | 10/2017 |
| EP | 3148419 | 1/2018 |
| GB | 1310949 | 3/1973 |
| GB | 1364127 | 8/1974 |
| GB | 2176313 | 12/1986 |
| GB | 2224957 | 5/1990 |
| GB | 2504284 A | 1/2014 |
| IN | 2005/000354 | 5/2006 |
| JP | 59113392 | 6/1984 |
| JP | H0623051 | 2/1994 |
| JP | 11033119 | 2/1999 |
| JP | 11286058 | 10/1999 |
| JP | 2001095920 | 4/2001 |
| JP | 2001-129091 A | 5/2001 |
| JP | 20011511507 | 8/2001 |
| JP | 2003139276 | 5/2003 |
| JP | 03194747 | 7/2003 |
| JP | 2003275312 | 9/2003 |
| JP | 2008132370 | 6/2008 |
| JP | 4242816 | 3/2009 |
| JP | 44022293 | 2/2010 |
| JP | 2011125618 | 6/2011 |
| JP | 11248076 | 12/2011 |
| JP | H 05208935 | 6/2013 |
| NZ | 527088 | 8/2001 |
| NZ | 564886 | 2/2011 |
| NZ | 587113 | 12/2011 |
| NZ | 586325 | 1/2012 |
| NZ | 583968 | 10/2012 |
| NZ | 597020 | 6/2013 |
| NZ | 600986 | 8/2013 |
| NZ | 604137 | 6/2014 |
| NZ | 610299 | 11/2014 |
| NZ | 630762 | 2/2016 |
| NZ | 625605 | 4/2016 |
| NZ | 710078 | 1/2017 |
| NZ | 710351 | 1/2017 |
| NZ | 631374 | 4/2017 |
| NZ | 631008 | 7/2017 |
| NZ | 733931 | 2/2019 |
| TW | 201245604 | 11/2012 |
| WO | WO 1996/020748 | 7/1996 |
| WO | WO 97/18001 | 5/1997 |
| WO | WO 1997/042475 | 11/1997 |
| WO | WO 2000/029057 | 5/2000 |
| WO | WO 2001/032069 | 5/2001 |
| WO | WO 01/41854 | 6/2001 |
| WO | WO 01/97894 | 12/2001 |

(56) References Cited

FOREIGN PATENT DOCUMENTS

| | | |
|---|---|---|
| WO | WO 2002/017991 | 3/2002 |
| WO | WO 02/066106 | 8/2002 |
| WO | WO 02/066107 | 8/2002 |
| WO | WO 2002/066106 | 8/2002 |
| WO | WO 2002/075854 | 9/2002 |
| WO | WO 2003/026721 | 4/2003 |
| WO | WO 2004/011072 | 2/2004 |
| WO | WO 2004/024429 | 3/2004 |
| WO | WO 2004/037330 | 5/2004 |
| WO | WO 2004/092955 | 11/2004 |
| WO | WO 2004/093954 | 11/2004 |
| WO | WO 2004/093955 | 11/2004 |
| WO | WO 2005/011785 | 2/2005 |
| WO | WO 2005/021076 | 3/2005 |
| WO | WO 2005/079670 A1 | 9/2005 |
| WO | WO 2006/017350 | 2/2006 |
| WO | WO 2006/019323 | 2/2006 |
| WO | WO 2007/019626 | 2/2007 |
| WO | WO 2007/043060 | 4/2007 |
| WO | WO 2007/051230 | 5/2007 |
| WO | WO 2008/055308 | 5/2008 |
| WO | WO 2008/056993 | 5/2008 |
| WO | WO 2008/058328 | 5/2008 |
| WO | WO 2008/060046 | 5/2008 |
| WO | WO 2008/060295 | 5/2008 |
| WO | WO 2008/076230 | 6/2008 |
| WO | WO 2008/097211 | 12/2008 |
| WO | WO 2009/002004 | 12/2008 |
| WO | WO 2009/006586 | 1/2009 |
| WO | WO 2009/022004 | 2/2009 |
| WO | WO 2009/127192 | 10/2009 |
| WO | WO 2009/146484 | 12/2009 |
| WO | WO 2010/031125 | 3/2010 |
| WO | WO 2010/031126 | 3/2010 |
| WO | WO 2010/091259 | 8/2010 |
| WO | WO-2011021708 A1 * | 2/2011 ........... B60H 3/0071 |
| WO | WO 2011/030251 A1 | 3/2011 |
| WO | WO 2011/059622 | 5/2011 |
| WO | WO 2012/053910 | 4/2012 |
| WO | WO 2012/065999 A2 | 5/2012 |
| WO | WO 2012/087644 | 6/2012 |
| WO | WO 2012/100291 | 8/2012 |
| WO | WO 2012/154883 | 11/2012 |
| WO | WO 2012/164407 | 12/2012 |
| WO | WO 2013/022356 A1 | 2/2013 |
| WO | WO 2013/026901 | 2/2013 |
| WO | WO 2013/045572 | 4/2013 |
| WO | WO 2013/045575 A1 | 4/2013 |
| WO | WO 2013/045586 | 4/2013 |
| WO | WO 2013/049660 | 4/2013 |
| WO | WO 2013/050907 A1 | 4/2013 |
| WO | WO 2013/088351 | 6/2013 |
| WO | WO 2013/127474 | 9/2013 |
| WO | WO 2013/137753 A1 | 9/2013 |
| WO | WO 2013/151447 | 10/2013 |
| WO | WO 2013/162386 | 10/2013 |
| WO | WO 2014/015382 | 1/2014 |
| WO | WO 2014/055407 | 4/2014 |
| WO | WO 2014/077706 | 5/2014 |
| WO | WO 2014/138804 | 9/2014 |
| WO | WO 2014/205513 | 12/2014 |
| WO | WO 2015/038013 A1 | 3/2015 |
| WO | WO 2015/060729 | 4/2015 |
| WO | WO 2015/119515 A1 | 8/2015 |
| WO | WO 2015/160268 | 10/2015 |
| WO | WO 2015/179916 | 12/2015 |
| WO | WO 2016/042522 | 3/2016 |
| WO | WO 2016/089224 | 6/2016 |
| WO | WO 2016/139645 | 6/2016 |
| WO | WO 2017/027906 | 2/2017 |
| WO | WO 2017/126980 | 7/2017 |

\* cited by examiner

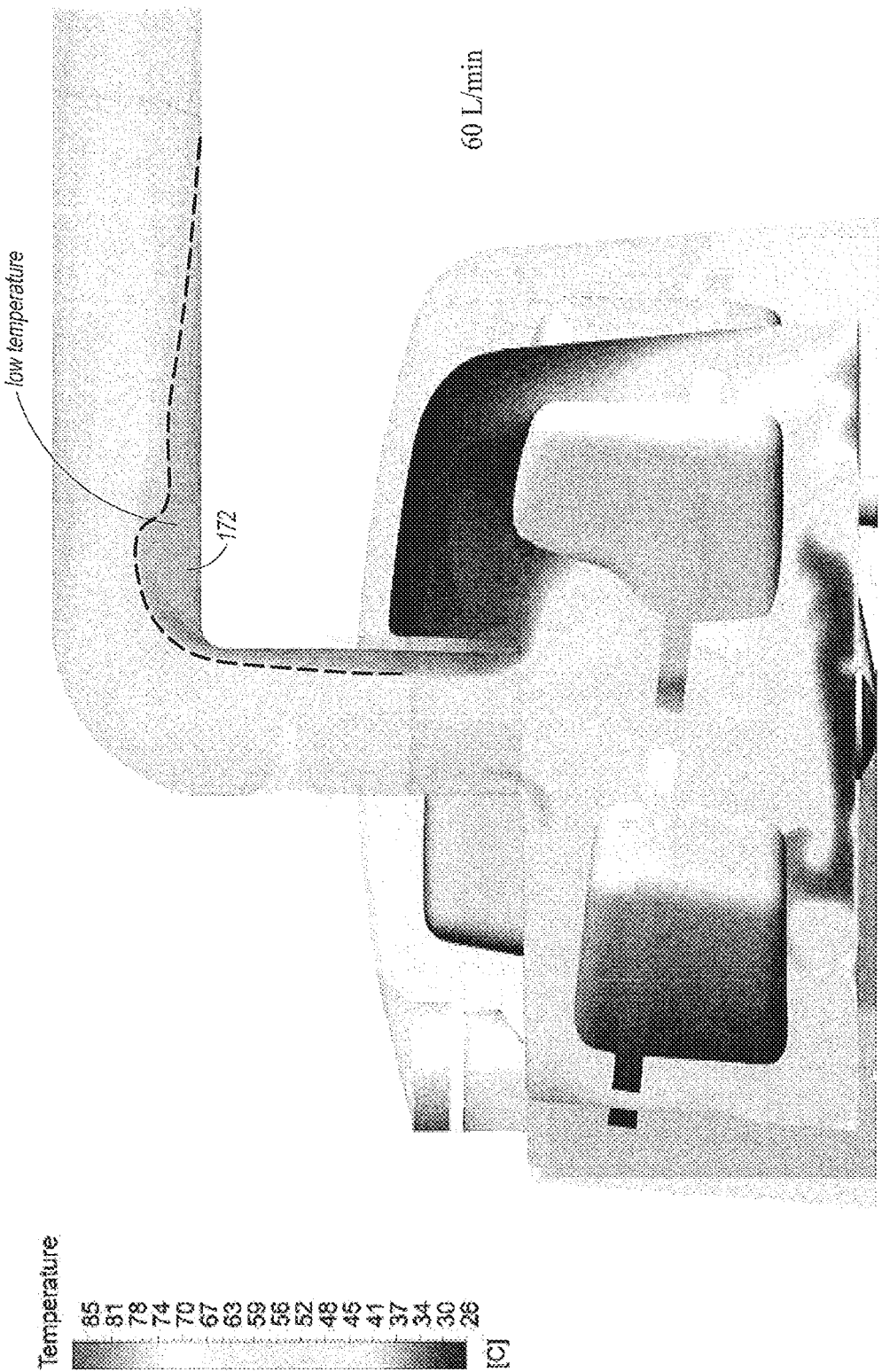

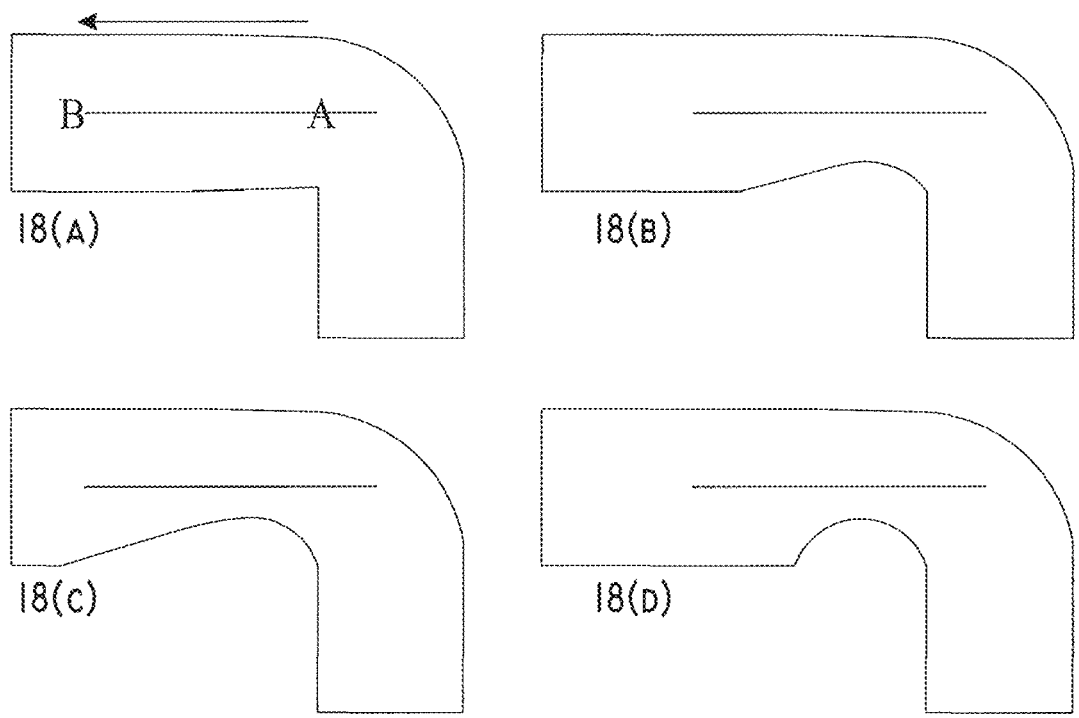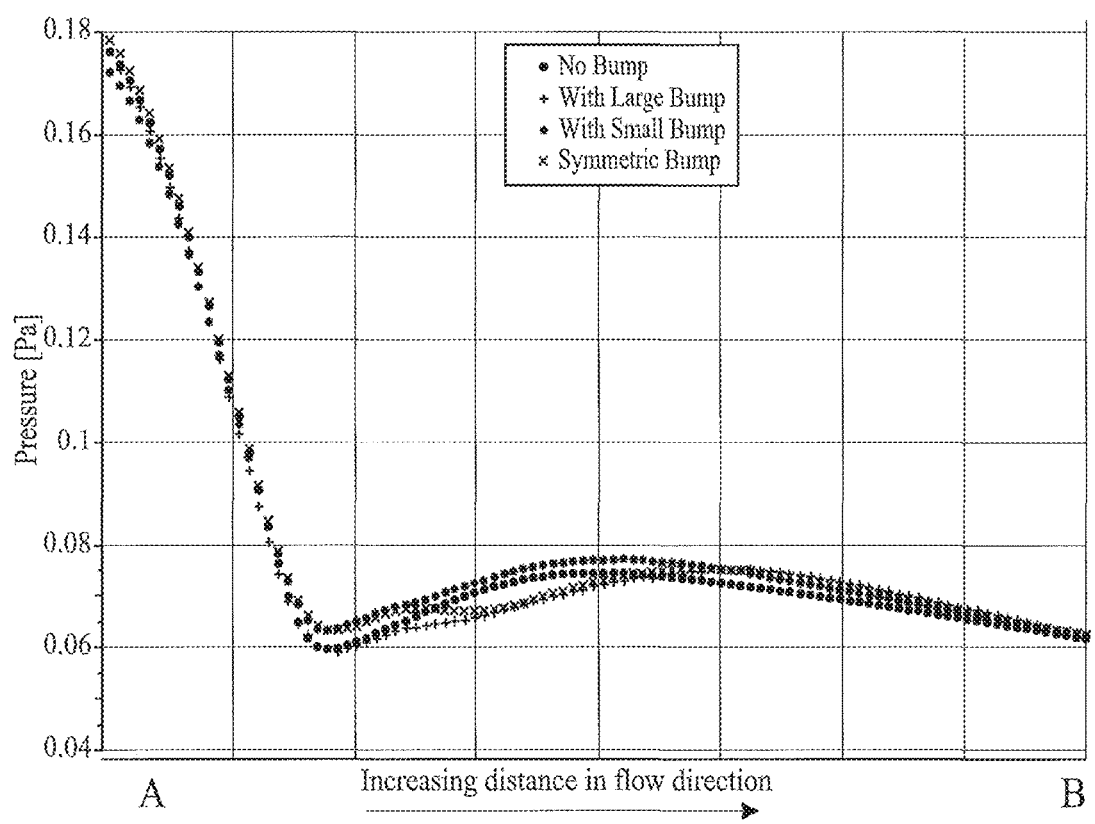
FIG. 18

RESPIRATORY HUMIDIFICATION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to humidification systems for providing humidified respiratory gases to patients. More particularly, the present disclosure relates to features that improve the performance of humidification systems.

Description of the Related Art

Respiratory humidification systems deliver heated and humidified gases to a patient via a patient interface. Patient interfaces can include a face mask, oral mask, nasal mask, nasal cannula, a combination of oral and nasal mask, tracheal mask, or the like. Gases leaving the humidification chamber to be delivered to a patient are at a temperature and relative humidity that may mimic the transformation of air that occurs as it passes through the nose to the lungs. This promotes efficient gas exchange and ventilation in the lungs, which aids defence mechanisms in the airways and increases patient comfort during treatment. Condensation within the humidification system can occur when gases with high humidity come into contact with a component having cooler walls.

SUMMARY

Delivery of humidified gases to patients exists in the prior art, however an aspect of at least one of the embodiments disclosed herein includes the realisation that there are problems with the delivery of this humidified gas. Horizontal connectors that connect between a humidification chamber and a conduit may allow condensate from the conduit or patient interface to run back into the humidification chamber in use. Elbow ports can be used to form a horizontal connection between a humidification chamber and a conduit, which can cause recirculation to occur resulting in stagnant zones, which cause greater heat loss to occur in these regions. This results in regions of low temperatures, which are more likely to form condensate. Condensate may also form at the connector, as this is an unheated section of the gas pathway. Condensate at the connector may form at the inner surface of the outer wall, before pooling at the base of the conduit, where it may flow back to the humidification chamber.

A system is disclosed which may improve the fluid characteristics of the respiratory gas. Thus, it may reduce the amount of condensate. In some configurations, certain aspects can reduce the amount of condensate that flows back to the humidification chamber relative to the prior art. In some configurations, the angle of the elbow port can be increased to greater than 90° to reduce the recirculation that causes stagnant zones to occur and thereby reduce the condensate that forms in the system. Some embodiments include an insert or other structure shaped as a raised portion, which can be located near the sharp corner of the elbow port, to fill at least some of the dead space that is formed due to the recirculation of gases that occurs. The insert may reduce the likelihood of recirculation occurring in this region and thus may reduce the likelihood of stagnant zones forming. Therefore, regions of low temperature and low velocity gas are reduced, which reduces the amount of condensate that is generated. A raised portion may also act as barrier to any condensate that is formed and, as such, reduce the likelihood of condensate flowing back to the humidification chamber. A raised portion may be added to the port of the humidification chamber, may be part of the connector that inserts when the connector is connected to the port, or may be part of the conduit.

Some embodiments may comprise either the humidification chamber outlet port or the conduit being shaped in such a way that, or including geometries such that, gravity may reduce the likelihood of condensate reaching the humidification chamber.

Therefore, the improved system may reduce condensate formation between the outlet port of the humidification chamber and the proximal conduit end by improving flow characteristics. The improved system may provide mechanisms to reduce the likelihood of condensate flowing back to the humidification chamber.

In some configurations, a respiratory humidification system comprises a humidification chamber that comprises an outlet port; a conduit that comprises a connector configured to engage with the outlet port such that the conduit forms a gases flow path from the humidification chamber; and a raised portion located in the gases flow path directly adjacent to a sharp corner disposed along the gases flow path within a region defined between the body of the humidification chamber and the conduit.

In some such configurations, the raised portion inhibits liquid flowing from the conduit to the humidification chamber in use.

In some such configurations, the raised portion fills or at least partially fills a dead space region in the gases flow path in use.

In some such configurations, the outlet port comprises a vertical section and a horizontal section and the connector is configured to engage with the horizontal section.

In some such configurations, the raised portion is located within the horizontal section of the outlet port.

In some such configurations, the outlet port comprises a vertical section, the connector comprises a vertical section and a horizontal section, and the vertical section of the connector is configured to engage with the outlet port.

In some such configurations, the raised portion is located within the horizontal section of the connector.

In some such configurations, the raised portion is directly attached to the outlet port.

In some such configurations, the raised portion is directly attached to the connector.

In some such configurations, the raised portion is attached to the conduit.

In some such configurations, the conduit comprises one or more heating elements.

In some configurations, a respiratory humidification system comprises a humidification chamber configured to contain a volume of liquid. The humidification chamber has an outlet port. A conduit is connectable to the outlet port of the humidification chamber. The conduit and the outlet port of the humidification chamber are connected by a connector. A gases flow path is defined from an entrance to the outlet port of the humidification chamber to an outlet of the conduit. A sharp corner is positioned along the gases flow path at a location where the gases flow path makes an abrupt change in direction. A raised portion is located in the gases flow path directly adjacent to the sharp corner.

In some such configurations, the raised portion is located immediately downstream from the sharp corner.

In some such configurations, the raised portion is located within a region of the gases flow path that would be a recirculation region without the raised portion present.

In some such configurations, the raised portion forms a portion of the outlet port.

In some such configurations, the raised portion forms a portion of the connector.

In some such configurations, the raised portion forms a portion of the conduit.

In some such configurations, the raised portion fills at least a lower portion of at least one of a horizontal portion of the outlet port, a conduit or a connector such that condensate is less likely to flow from the conduit into the humidification chamber.

In some such configurations, the raised portion has a tapered edge.

In some such configurations, the raised portion has a straight edge.

In some such configurations, the raised portion is asymmetrical along its length.

In some such configurations, the raised portion is symmetrical along its length.

BRIEF DESCRIPTION OF THE DRAWINGS

These and other features, aspects, and advantages of the present disclosure will be described with respect to the following figures, which are intended to illustrate and not to limit the preferred embodiments.

FIG. 12 shows a temperature profile of a humidification chamber with an elbow port for a 60 L/min flow.

FIG. 18 is a plot comparing pressure magnitudes taken along a horizontal line that extends along an axis of the configurations of FIGS. 13(a)-13(d).

DETAILED DESCRIPTION OF THE PREFERRED EMBODIMENT

Figure 1:
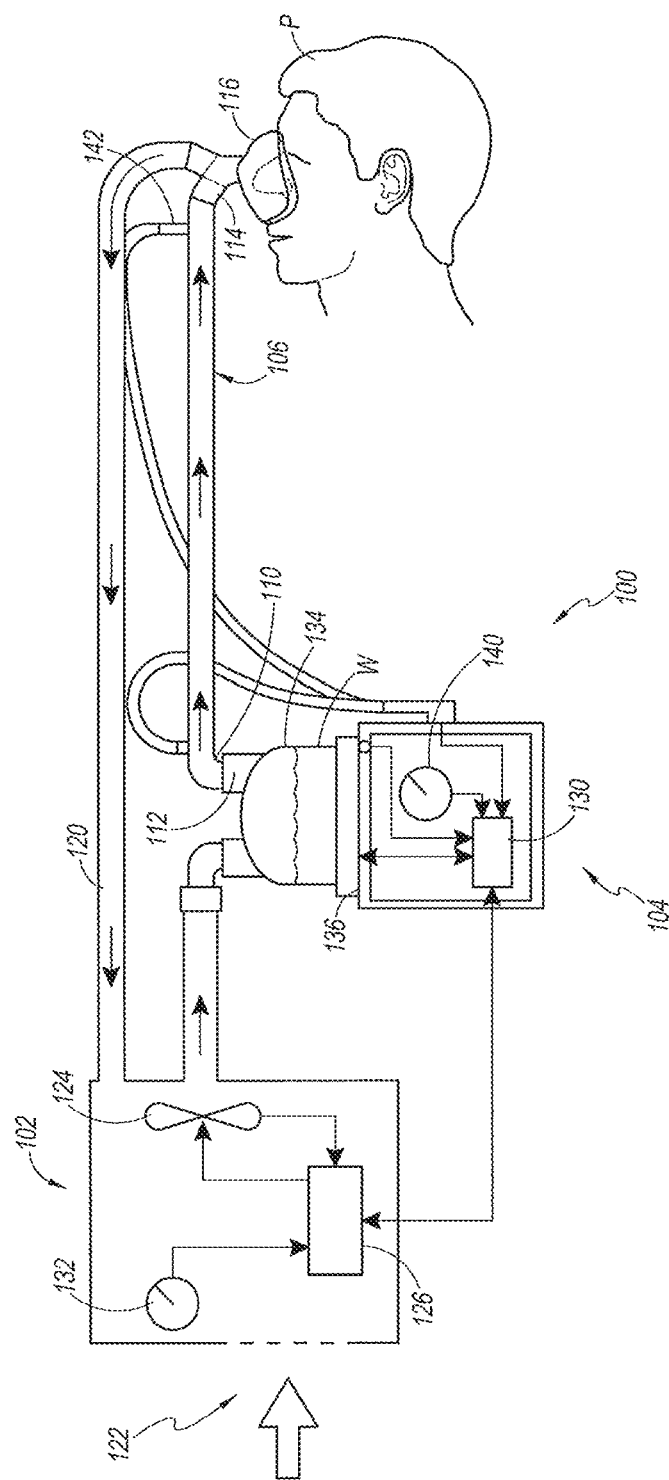
FIG. 1 is a schematic view of an example embodiment of a patient gas supply system.

With reference to FIG. 1, a system 100 is illustrated that can be used to supply heated and/or humidified gases flow to a patient or other user. The system 100 can be configured to be a continuous, variable, or bi-level positive airway pressure (PAP) system, invasive or non-invasive respiratory assistance system, high flow respiratory therapy system, a surgical insufflation system, or a system providing other forms of medical gases. The system 100 may be readily adapted for other applications involving the supply of a heated and/or humidified gas flow to a user or patient, including but not limited to laparoscopy, ventilation support, and the like. Such applications may use alternative gases, operating parameters (e.g., flow, pressure, temperature, or humidity) and patient interfaces.

In the system 100, dry or relatively dry gases pass from a gases source 102 to a humidifier 104. The gases source 102 may be, for example, a ventilator or a blower.

The humidifier 104 conditions the dry or relatively dry gases. For example, the humidifier 104 can supply heat or humidity to the dry or relatively dry gases.

An inspiratory tube 106 is used to deliver the conditioned gases to a patient P. In the illustrated configuration, a distal end 110 of the inspiratory tube 106 connects to a port 112 of the humidifier 104. Thus, the humidifier 104 supplies conditioned gases to the inspiratory tube 106.

In the illustrated configuration, the conditioned gases flow through the inspiratory tube 106 to a Y-piece 114. A patient interface 116 (e.g., a mask) receives the conditioned gases from the Y-piece 114 and the patient interface 116 supplies the conditioned gases to the patient P. Any suitable patient interface may be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks, oral masks, nasal masks, a combination of oral and nasal mask, for example), cannulas (nasal cannulas, for example), and nasal pillows.

In the illustrated configuration, an expiratory tube 120 also connects to the patient interface 116 through the Y-piece 114. The expiratory tube 120 may be configured to move exhaled gases away from the patient P. In the illustrated configuration, the expiratory tube 120 returns exhaled gases from the patient P to the gases source 102.

In illustrated configuration, dry or relatively dry gases enter the gases source 102 through a vent 122 or other inlet. A fan, blower or other flow generator 124 may improve gas flow into the gases source 102 by drawing air or other gases through the vent 122. The flow generator 124 may be, for instance, a variable speed fan.

An electronic controller 126 controls the speed of the flow generator 124. In particular, the function of the electronic controller 126 may be controlled by an electronic master controller 130 in response to inputs to the master controller 130 and a user-set predetermined required value (e.g., a preset value) of pressure or fan speed. The value can be set using an input component, such as a dial 132, for example but without limitation.

The humidifier 104 comprises a humidification chamber 134. The humidification chamber 134 comprises the port 112. The body of the humidification chamber 134 can contain a volume of water W or other suitable humidifying liquid. The humidification chamber 134 is removable from the humidifier 104 after use to allow the humidification chamber 134 to be more readily sterilized or disposed.

The body of the humidification chamber 134 may be formed from a non-conductive glass or plastics material. The humidification chamber 134 may comprise conductive components. For instance, the humidification chamber 134 may comprise a highly heat-conductive base (for example, an aluminum base). The heat-conductive base can contact or associate with a heater plate 136 on the humidifier 104.

The humidifier 104 may also include electronic controls. In the illustrated configuration, the humidifier 104 includes the master controller 130. The master controller 130 can be an electronic, analog, or digital master controller. The master controller 130 may be a microprocessor-based controller executing computer software commands stored in associated memory. In response to humidity or temperature values provided via a user interface 140, for example, and other inputs, the master controller 130 determines when (or to what level) to energize the heater plate 136 to heat the water W within the humidification chamber 134.

A sensor probe 142 may connect to the inspiratory tube 106 near the Y-piece 114, or directly to the Y-piece 114 or the patient interface 116. The sensor probe 142 monitors the temperature of the flow of gases near or at the patient interface 116. A heating filament (not shown) may be used to adjust the temperature of the patient interface 116, the Y-piece 114, and/or the inspiratory tube 106 to raise or maintain the temperature of the flow of gases above the saturation temperature, thereby reducing the opportunity for unwanted condensation.

In FIG. 1, exhaled gases are returned from the patient interface 116 to the gases source 102 via the expiratory tube 120. The expiratory tube 120 may have a sensor probe and/or heating filament, as described above with respect to the inspiratory tube 106, integrated with it to reduce the opportunity for condensation. Furthermore, the expiratory tube 120 need not return exhaled gases to the gases source 102. Alternatively, exhaled gases may be passed directly to ambient surroundings or to other ancillary equipment, such as an air scrubber/filter (not shown). In certain embodiments, the expiratory tube 120 is omitted altogether.

Figure 2:
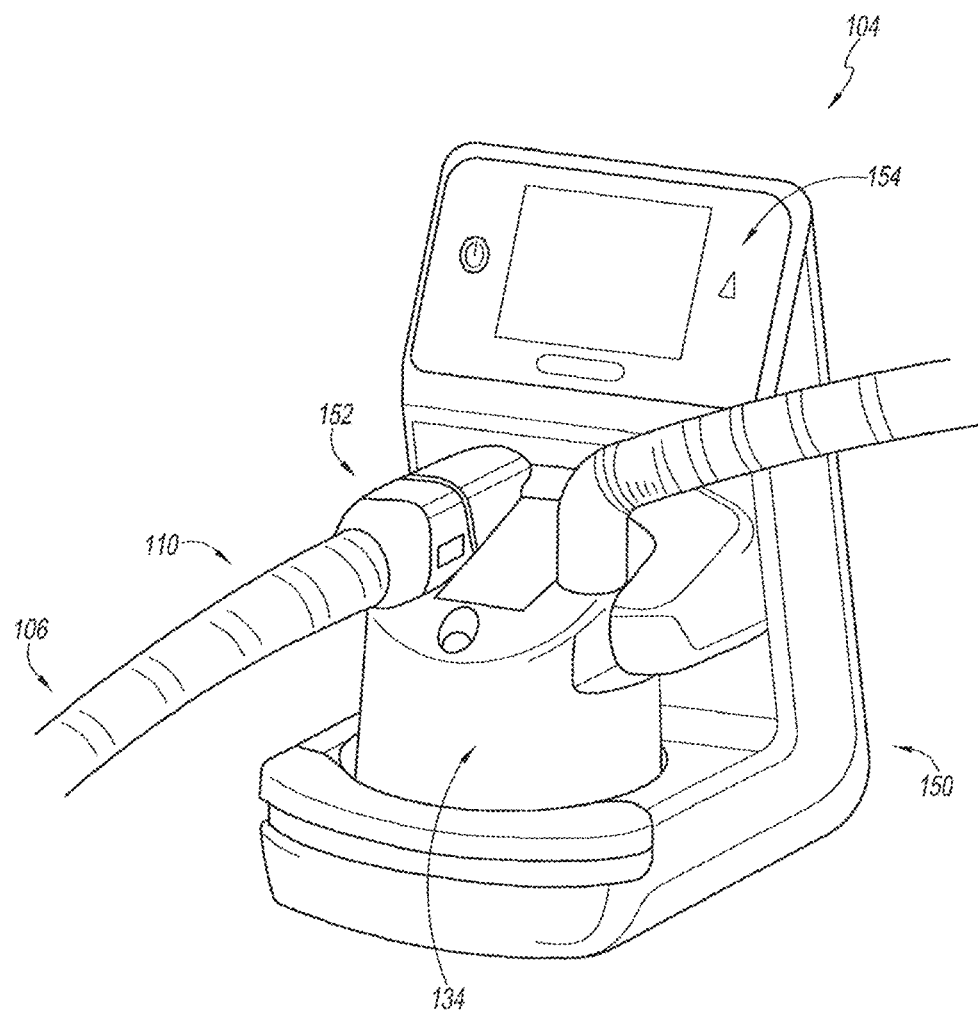
FIG. 2 is a perspective view of a humidifier useable in the system of FIG. 1.

With reference to FIG. 2, a humidification apparatus 150 that can be used as the humidifier 104 in the system 100 is shown. As illustrated, a connector 152 pneumatically connects the distal end 110 of the inspiratory tube 106 to the port (not shown) of the humidification chamber 134. The connector 152 may also facilitate electrical connection to the humidifier 104. The conduit 106 may comprise one or more resistive heating wires that provide for heating of gases flowing through the conduit 106 and/or sensor wires that electrically or otherwise facilitate communication of signals relating to one or more parameters of the system 100. Thus, the term "electrical connection" is used to distinguish from "pneumatic connection" and should not be construed in a limiting way.

The humidifier 104 further includes a panel 154. The panel 154 may be used to mount a user display and/or controls. For example, various dials, switches, and other input means may be used to control operation of the device. Additionally or alternatively, a touch screen display may be used. The user display may display parameters of the system 100, warnings in the event of any errors or malfunctions, or prompts where user action is required, etc. Where a touch screen display is used, the same display may be used to present information to a user and receive inputs from a user, at least in part.

Figure 3:
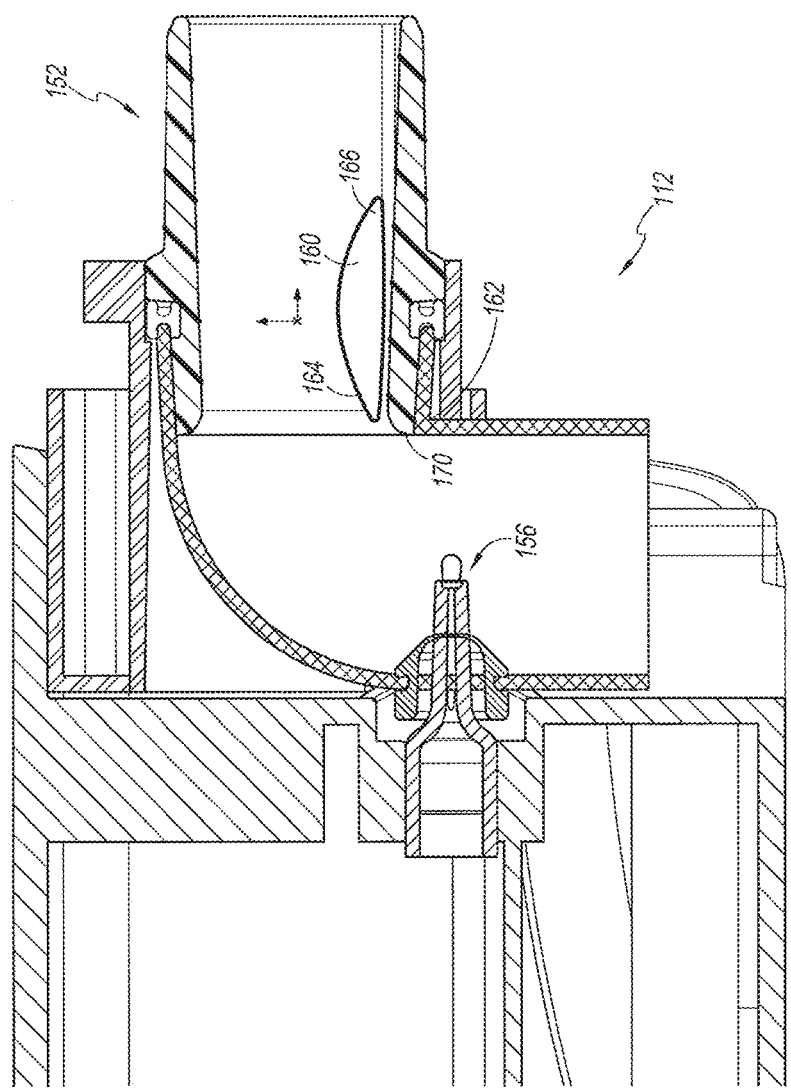
FIG. 3 in an enlarged section view of a portion of the humidifier of FIG. 2 and showing a first configuration of a raised portion within the gases flow path.

As illustrated in FIG. 2, the conduit 106 is mounted to the humidification chamber 134 such that the conduit 106 extends substantially parallel to the direction of motion of the humidification chamber 134 as it is slid on or off of the humidifier 104. With reference to FIG. 3, a sectioned view of a portion of the humidifier 104 is shown. As shown, a probe 156 can be positioned within the outlet port 112 upstream of the connector 152 that connects the chamber 134 to the inspiratory tube 106. In some configurations, the probe 156 can be positioned in the port 112. In some configurations, the probe 156 can be positioned within the connector 152. In some configurations, the port 112 is formed as an elbow with a vertically extending portion and a horizontally extending portion. Other configurations are possible.

In configurations with the elbow port 112 having a sharp corner, it has been discovered that a significant amount of recirculation occurs in the horizontal portion of the port 112. More particularly, with reference to FIGS. 7-12, a sharp corner at the inside lower transition from vertical to horizontal causes a significant amount of recirculation within the flow. This recirculation, in effect, creates a significant region of dead space. The gases flow can cool within the recirculation/dead space region, which can cause condensation to occur within this region.

FIGS. 7-12 show examples of the velocity and temperature profiles that can be generated for flow rates of 5 L/min, 30 L/min and 60 L/min respectively. The system 100 is not limited to these flow rates: they merely provide an indication of the relationship between different flow rates and the generated fluid characteristics. It appears that a larger dead space region may be generated at higher flow rates.

The system 100 disclosed herein may improve the fluid characteristics of the respiratory gas and may reduce the amount of condensate or other fluid that flows back to the humidification chamber 134 from the attached conduit 106. To improve the fluid characteristics in the system 100, the angle of the elbow port 112 of the humidification chamber 134 may be increased: this may soften the sharp corner that is shown in FIGS. 7-12.

Figure 4:
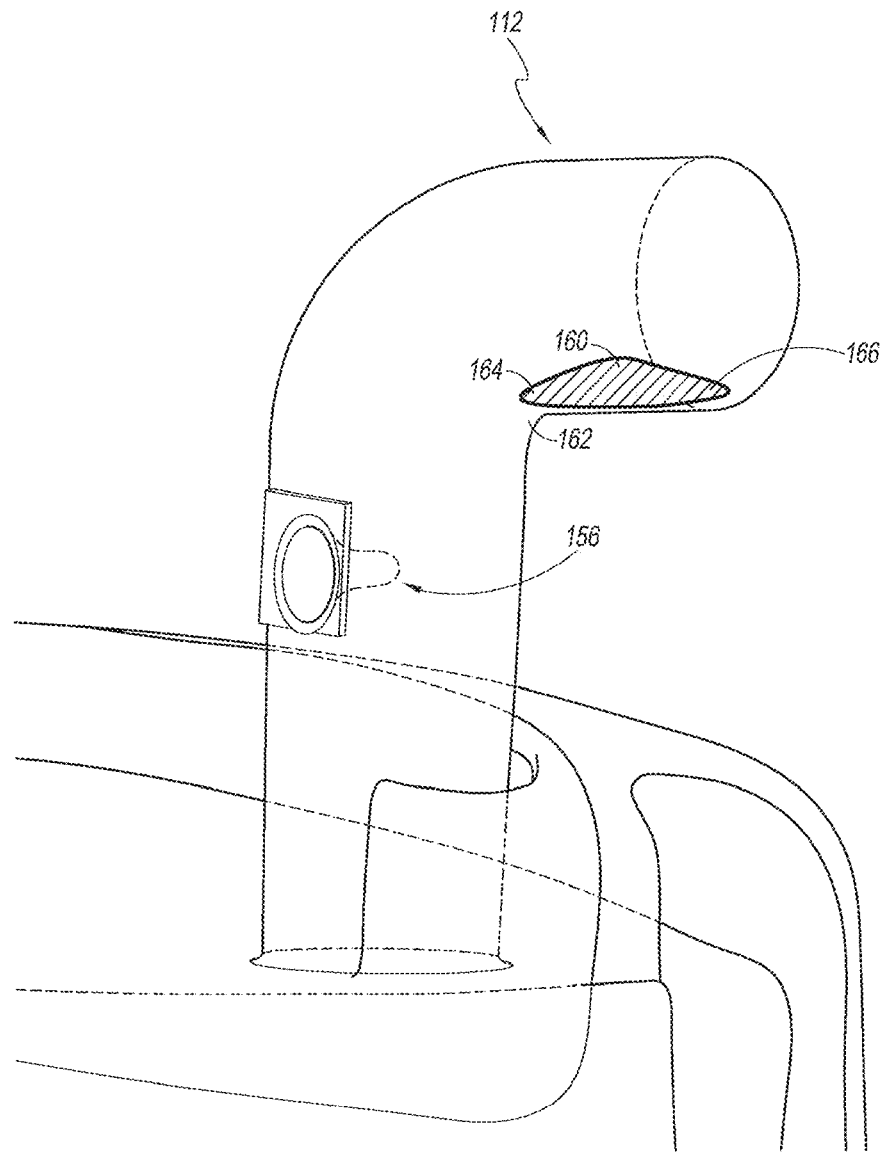
FIG. 4 is a view of a portion of a humidifier chamber useable with the humidifier of FIG. 2 and showing a second configuration of a raised portion within the gases flow path.

With reference again to FIG. 3, a raised portion (or insert) 160 can be attached to, or integrally formed with, one or more components of the system 100. For example, the raised portion 160 is shown in FIG. 3 as being positioned within the connector 152. By way of another example, the raised portion 160 is shown in FIG. 4 as being positioned within the port 112. In some configurations, the raised portion 160 can be positioned within the inspiratory conduit 106 or the like. The raised portion 160 may be inserted or added to a component using moulding techniques, adhesives, or other appropriate ways of attachment.

In some configurations, an elbow portion 162 can be defined at the transition from a first direction to a second direction of the port 112. In some configurations, the elbow portion 162 is defined by a transition from a first direction to a second direction that is generally normal to the first direction. In some configurations, the elbow portion 162 is defined by a transition from vertical to horizontal.

As shown in FIG. 3 and FIG. 4, the raised portion 160 can be positioned directly adjacent to the elbow portion 162. As used herein, directly adjacent has its ordinary meaning of sharing a border or boundary. In some configurations, the raised portion 160 is positioned within the gas flow of only one of the two portions of the port 112. In other words, in the illustrated configurations, the raised portion 160 protrudes into the gas flow path of the horizontal portion but does not protrude into the gas flow path of the vertical portion. In some configurations, at least the upstream end 164 of the raised portion 160 is positioned entirely within a region that would be a recirculation region without the raised portion 160 present. In some such configurations, both the upstream end 164 and the downstream end 166 of the raised portion 160 are positioned within a region that would be a recirculation region without the raised portion 160 present. In some configurations, the entire raised portion 160 is positioned within a region that would be a recirculation region without the raised portion 160 present. In some configurations, the raised portion 160 is located in the gases flow path directly adjacent to a sharp corner 170 created by the angle of the elbow portion 162 disposed along the gases flow path within a region defined between the humidification chamber 134 and the conduit 106. In some configurations, the sharp corner 170 is positioned along the gases flow path at a location where the gases flow path makes an abrupt change in direction.

Figure 5:
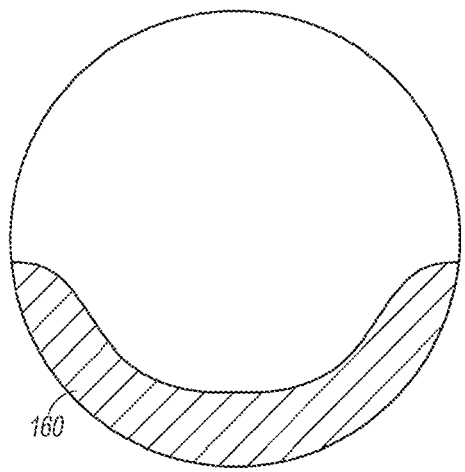
FIGS. 5 and 6 show cross-sections of raised portions.
Figure 6:
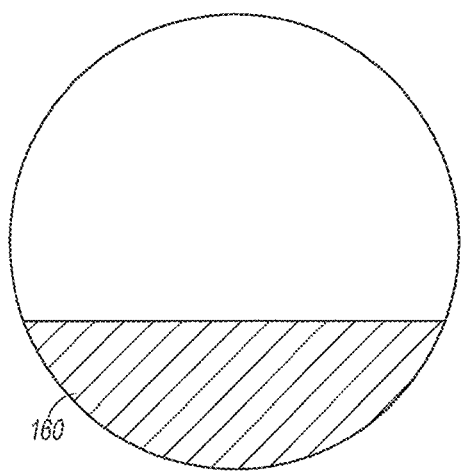
Figure 7:
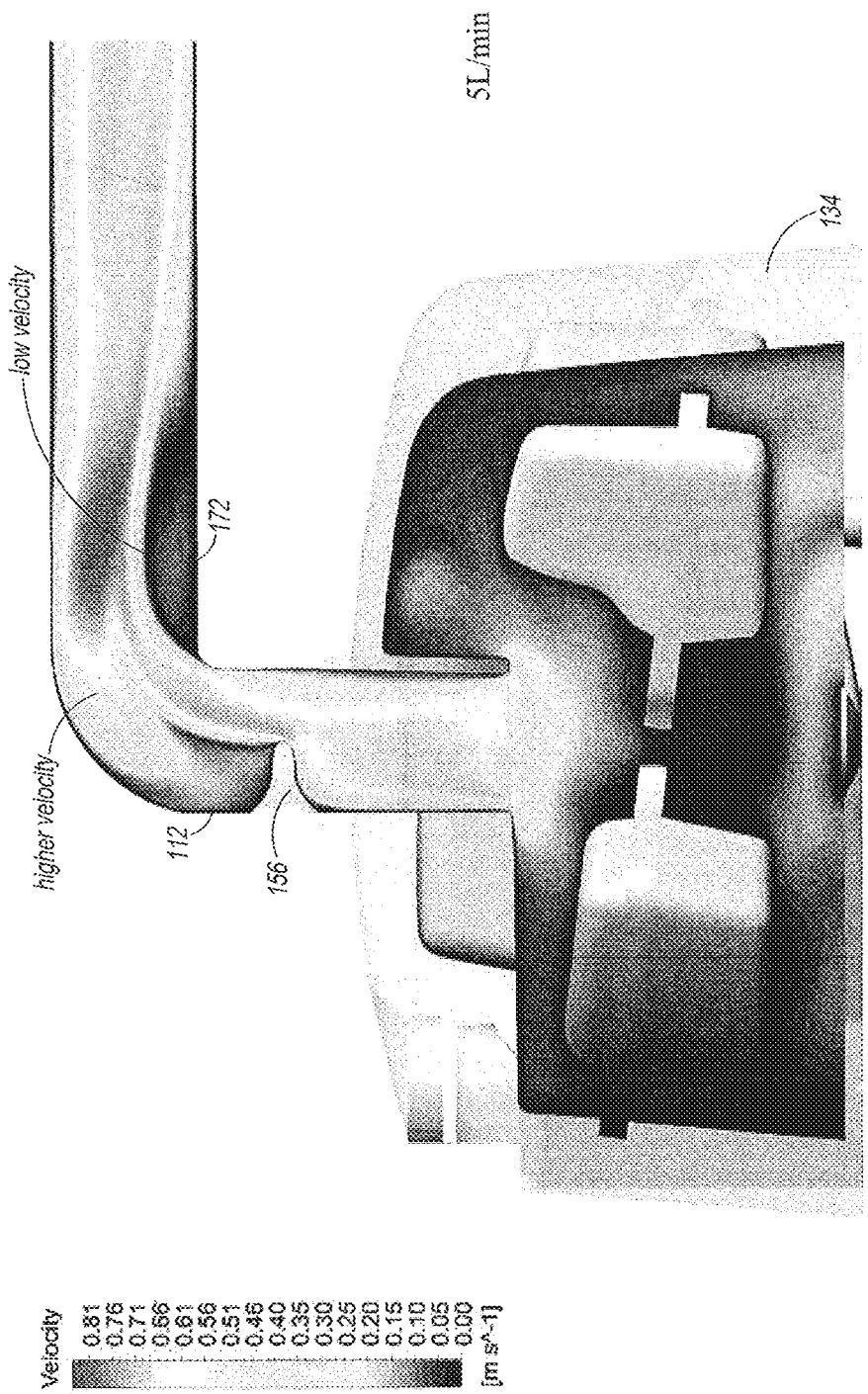
FIG. 7 shows a velocity profile of a humidification chamber with an elbow port for a 5 L/min flow.
Figure 8:
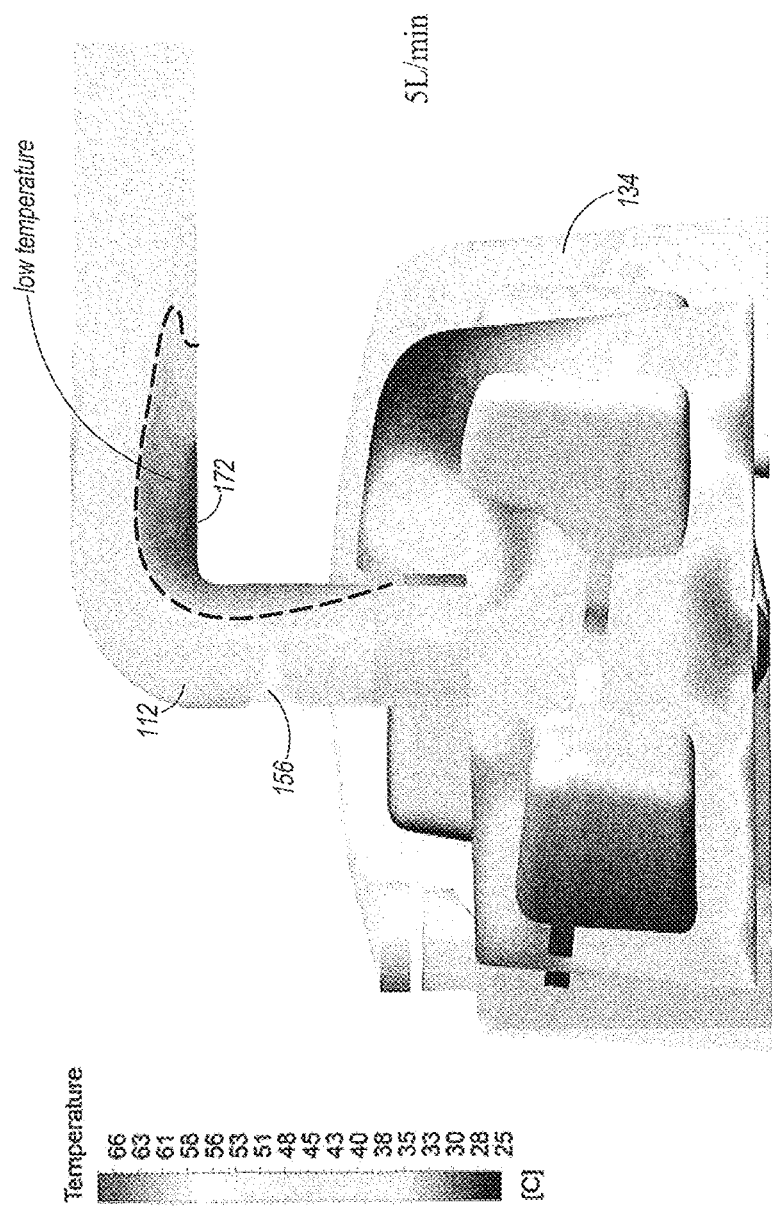
FIG. 8 shows a temperature profile of a humidification chamber with an elbow port for a 5 L/min flow.
Figure 9:
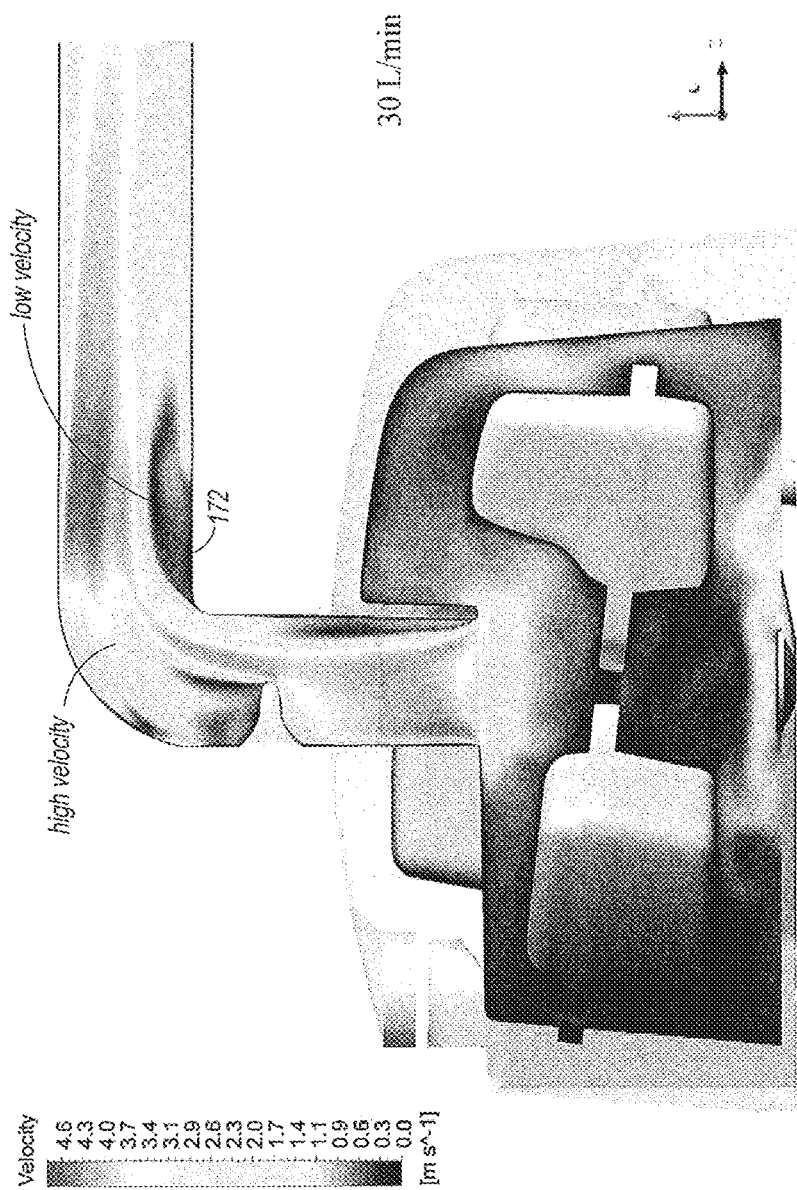
FIG. 9 shows a velocity profile of a humidification chamber with an elbow port for a 30 L/min flow.
Figure 10:
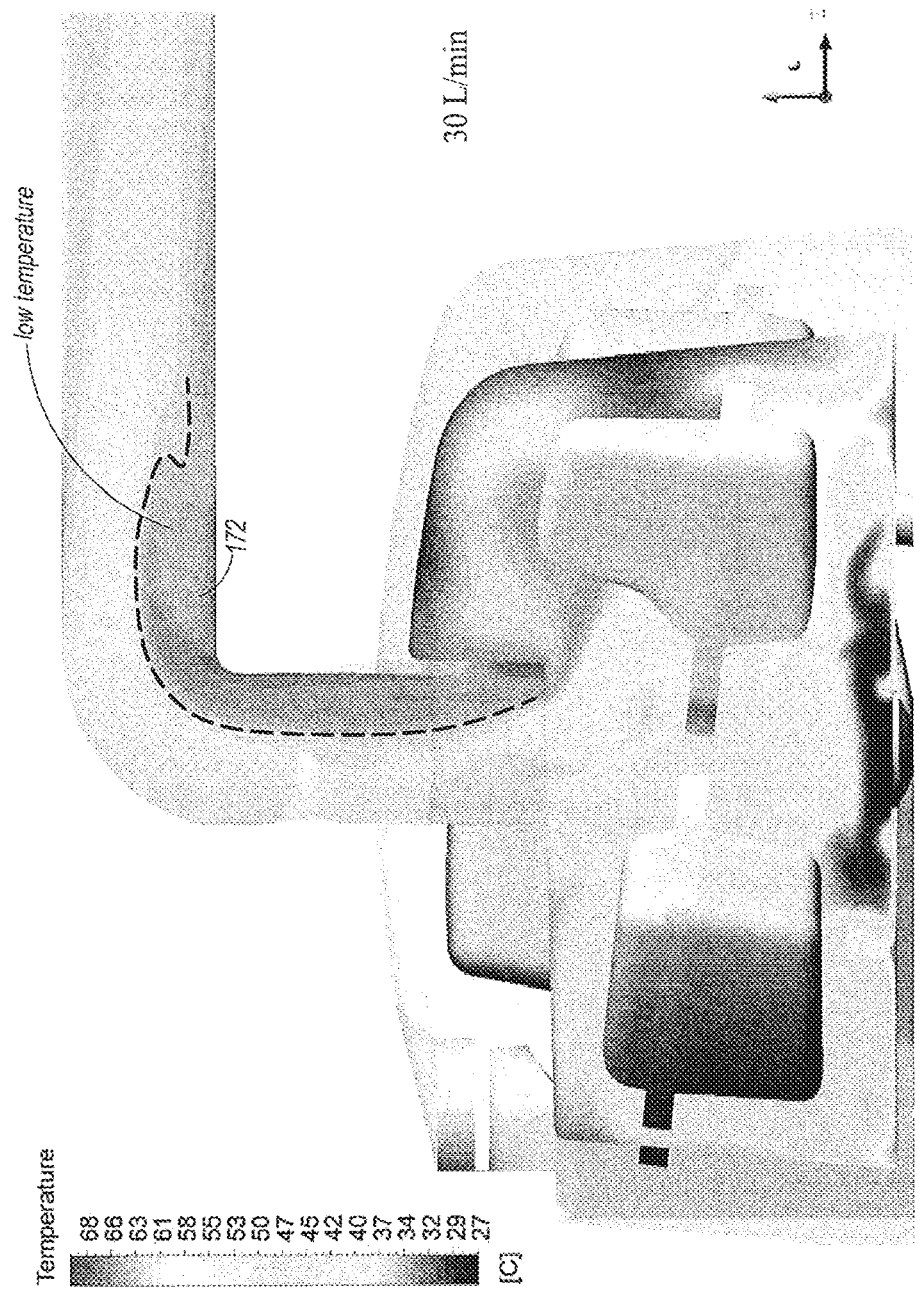
FIG. 10 shows a temperature profile of a humidification chamber with an elbow port for a 30 L/min flow.
Figure 11:
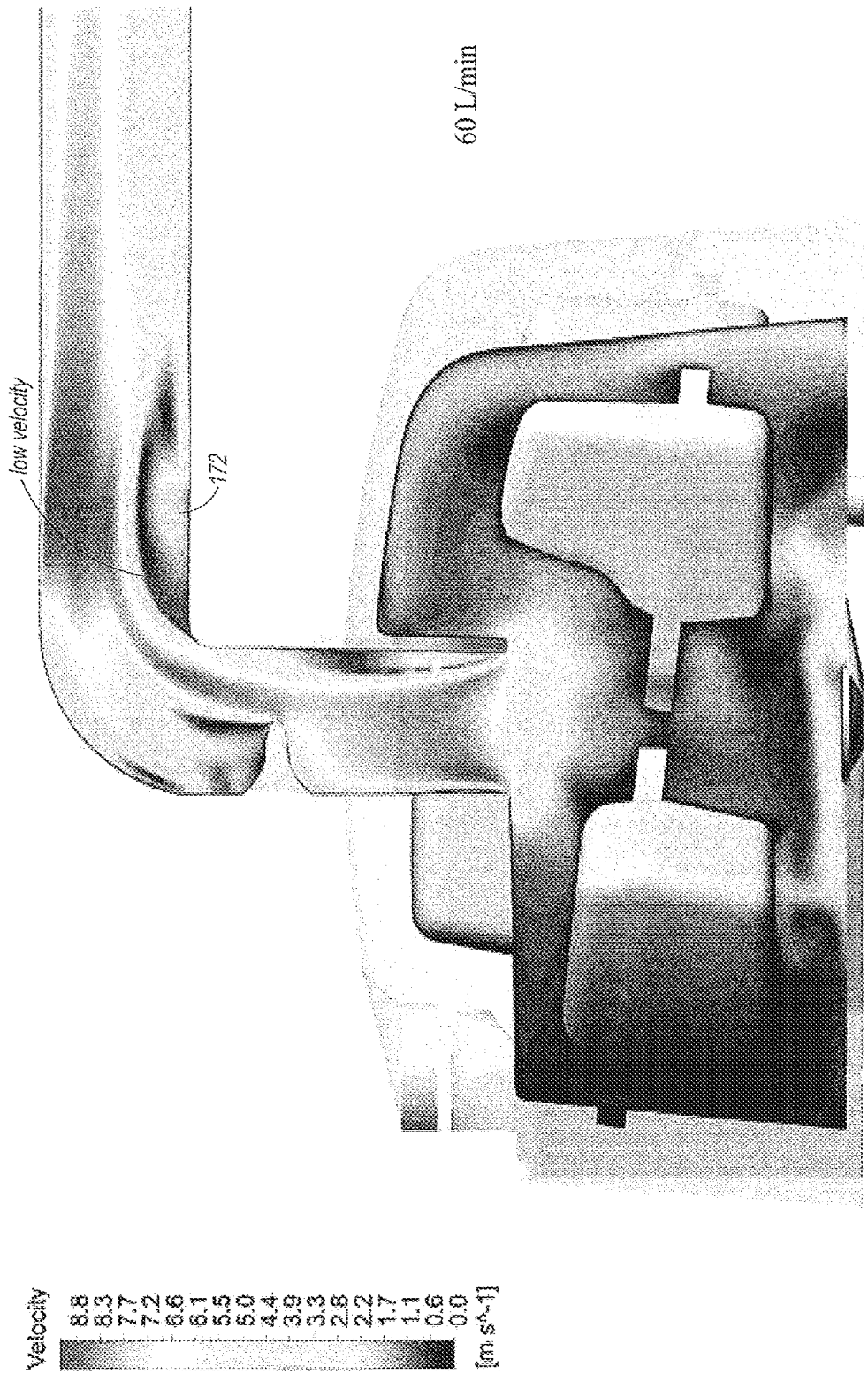
FIG. 11 shows a velocity profile of a humidification chamber with an elbow port for a 60 L/min flow.

With reference now to FIG. 5 and FIG. 6, the raised portion 160 may resemble a speed bump, protrusion, insert, or the like. The raised portion 160 can be integrally formed with the port 112, the connector 152, or another component that joins the humidification chamber 134 and the inspiratory conduit 106. The raised portion 160 can be a separate and/or separable component from the port 112, the connector 152, or other component and secured thereto in any suitable manner.

As shown in FIG. 4, the raised portion 160 is attached to the outlet port 112 of the humidification chamber 134. The outlet port 112 comprises the elbow portion 162, which, in this case, creates an angle of, but not limited to, 90°. The raised portion 160 is located at or near the sharp corner 170 created by the angle of the elbow portion 162 because the fluid may be more likely to follow the surface of the port 112 if it is a smooth curve.

The size of the raised portion 160 can be determined by the temperature and velocity profiles, examples of which are shown in FIGS. 7-12, which estimate the size of a dead space region 172 present in the system 100 at high flows. As discussed above, the dead space region 172 may appear to be larger at higher flow rates and, therefore, if the raised portion 160 is made to accommodate these flow rates, it may also accommodate lower flow rates. Occlusion of flow is less likely to occur at lower flow rates and, because the raised portion 160 fills the regions of otherwise dead space present in the system 100, there are minimal limitations of flow. Thus, the raised portion 160 may accommodate higher flow rates, although, in some embodiments, lower flow rates may also be accommodated. The system 100 discloses the use of the raised portion 160 to accommodate flows between about 5 L/min and about 60 L/min. Some embodiments may accommodate flow rates that exceed these values, for example between 0 L/min and about 100 L/min.

FIG. 3 shows the raised portion 160 inserted into the port 112 as the connector 152 is connected with the humidification chamber port 112. The raised portion 160 may be attached to the connector 152, the raised portion 160 may be attached to the conduit 106 or, in some embodiments, the raised portion 160 may act as a tongue that may be attached to the connector 152 or the conduit 106 and that may extend past the edge of the connector 152 into the outlet port 112. In some embodiments, the connector 152 may be a male connector that is used with the raised portion 160 attached at the edge of the connector 152. This is not considered to be an exhaustive list of mechanisms to insert the raised portion 160 into the port 112 of the humidification chamber 134, but merely a listing of examples of mechanisms that could be used, recognising that other mechanisms may also be possible.

The raised portion 160 may be located near the sharp corner 170 to soften the sharp corner 170 and to fill at least a portion of, if not the entirety of, the dead space region 172 that is formed (see FIGS. 7-12). Benefits of inserting the raised portion 160 into the port 112 of the humidification chamber 134 as the connector 152 is inserted include the reduced distance between the outlet port 112 of the humidification chamber 134 and the conduit 106. This may be beneficial because the connector 152 itself is unheated, which allows the gas to cool therein, which can cause the formation of condensate as the gas travels between the outlet port 112 of the humidification chamber 134 and the conduit 106. By reducing the distance between the outlet port 112 of the humidification chamber 134 and the heated portion of the conduit 106, the time available for gas cooling may be reduced. As a result, the amount of condensate that is formed may also be reduced.

The raised portion 160 may also act to occlude some or all of any condensate or other liquid flowing back into the humidification chamber 134. By filling at least a portion of the dead space 172, the lower temperature zone of recirculation can be reduced and, thus, it is likely that less condensate is generated due to the reduced flow separation that may be produced. This may improve the temperature profile of the gas over the unheated connector 152 as it moves towards the heated conduit 106, which may result in less temperature loss as it passes through the unheated connector 152.

FIG. 5 and FIG. 6 show possible cross sections of the raised portion 160, such as that discussed above. FIG. 5 shows the raised portion 160 having a tapered edge while FIG. 6 shows the raised portion 160 having a straight edge. Other configurations also are possible.

With reference to FIGS. 13(*a*)-13(*d*), several different configurations that have been investigated are illustrated. Note that FIGS. 13(*a*)-13(*d*) are depictions of the gases flow path and, as such, the raised portion 160 is not explicitly shown and the conduit 106, the connector 152, and the port 112 also are not explicitly shown. Rather, these illustrations simply reflect the gas flow path defined by these boundary components.

FIG. 13(*a*) illustrates a configuration without any raised portion. FIG. 13(*a*), however, is useful to establish a baseline and to explain some of the dimensions used in the following discussion. As illustrated, the flow path has an outlet diameter $d_1$ and an inlet diameter $d_2$. In some configurations, the outlet diameter and the inlet diameter are the same. In some configurations, the outlet diameter $d_1$ is larger than the inlet diameter $d_2$ (i.e., the conduit 106 has a larger bore diameter than the port 112). In the illustrated configurations, the inlet diameter $d_2$ is 20 mm while the outlet diameter $d_1$ is 21 mm.

Also, in the illustrated configurations, the radius r between the inlet portion and the outlet portion is 10 mm. In each of the configurations shown in FIGS. 13(a)-13(d), these basic dimensions are the same.

Figure 13A:
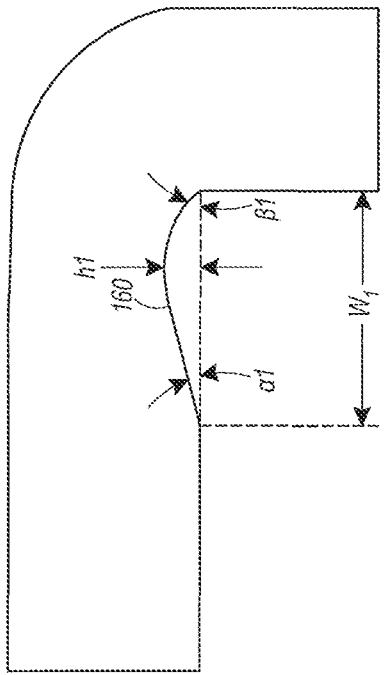
FIGS. 13(a)-13(d) show different configurations of gas flow paths with three different raised portions illustrated in FIGS. 13(b)-13(d).
Figure 13B:
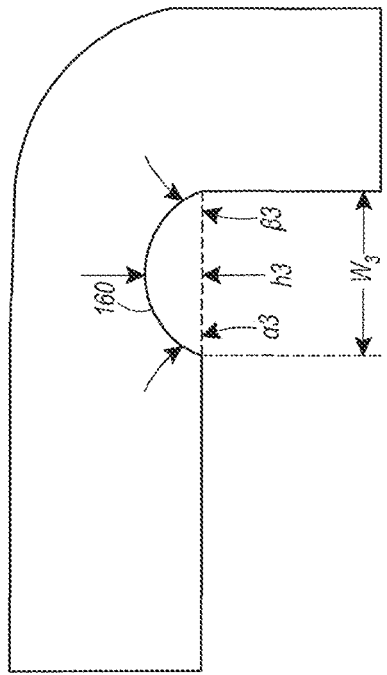
Figure 13C:
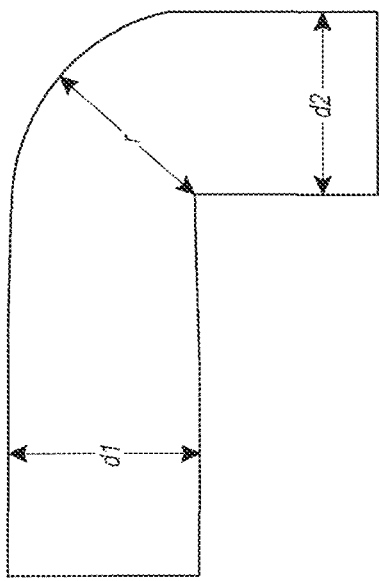
Figure 13D:
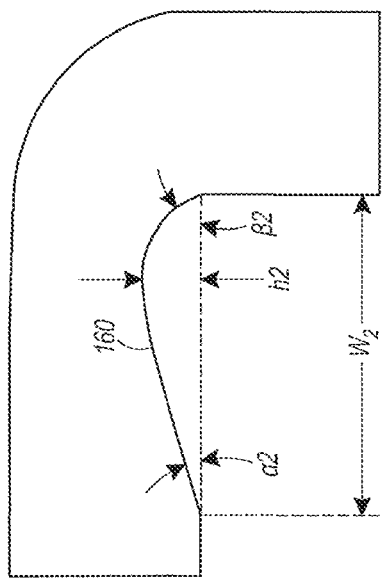
Figure 14B:
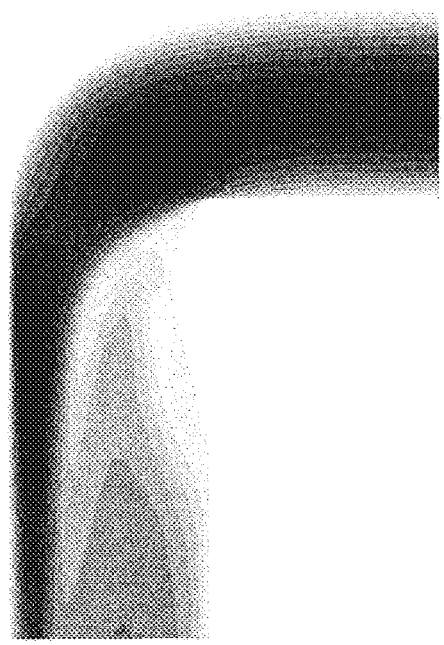
FIGS. 14(a)-14(d) illustrate flow velocity contours through the configurations of FIGS. 13(a)-13(d) for a 5 L/min flow.
Figure 14D:
Figure 14A:
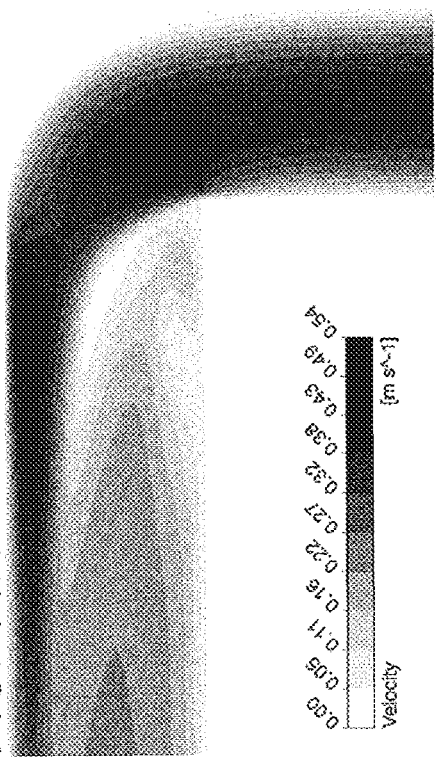
Figure 14C:
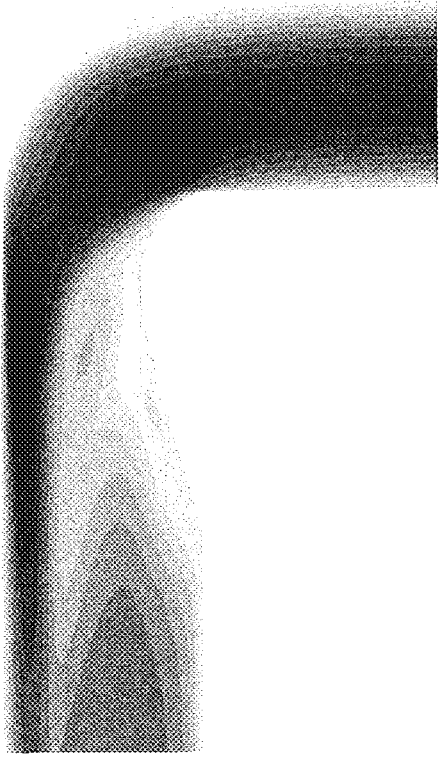
Figure 15B:
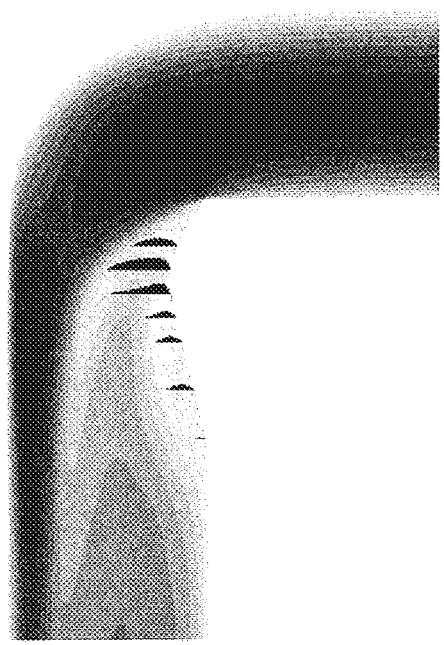
FIGS. 15(a)-15(d) illustrate reverse flow vectors overlaid onto the flow velocity contours of FIGS. 14(a)-14(d).
Figure 15D:
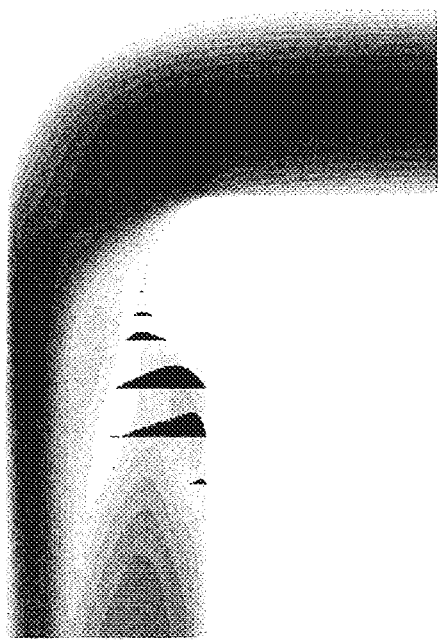
Figure 15A:
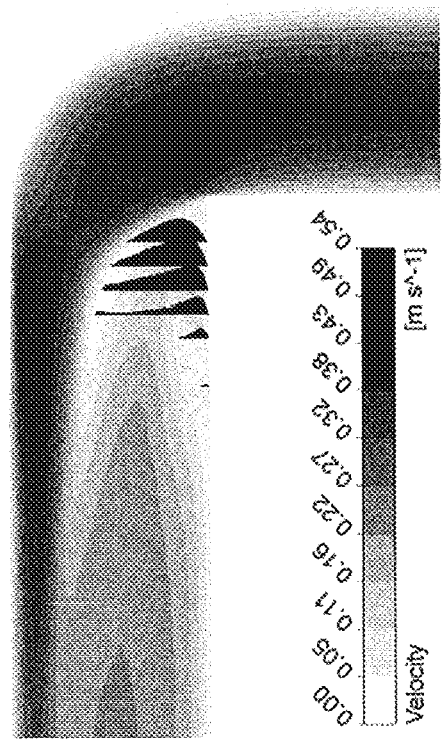
Figure 15C:
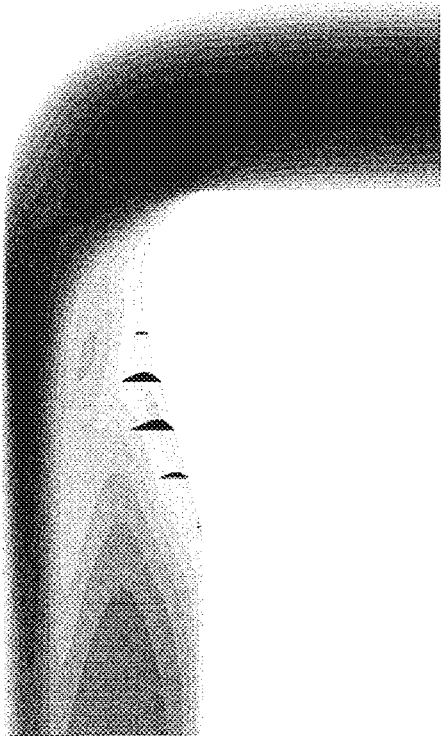

FIG. 13(b) illustrates a smaller asymmetric embodiment of the raised portion 160. FIG. 13(c) illustrates a larger asymmetric embodiment of the raised portion 160. FIG. 13(d) illustrates a symmetric embodiment of the raised portion 160. With reference to FIGS. 13(b), 13(c), and 13(d), each of the raised portions 160 can be generally defined in section with the illustrated dimensions. Each of the raised portions 160 will have a first angle ($\alpha$) at the downstream end 166, a second angle ($\theta$) at the upstream end 164, a length (w) and a height (h). A volume reduction in the flow path in the region of the raised portions 160 can be defined as the volume of the raised portion 160 divided by the volume of the cylinder bounded by the length (w) of the raised portion 160 and the outlet diameter (d1).

In some configurations, the first angle ($\alpha$) can be determined once the other dimensions have been determined. For example, in some configurations, the height (h) can be between 15% and 30% of the outlet diameter d1. The second angle ($\theta$) can be between 30° and 60°. The length (w) can be larger than 18 mm. Thus, the upper limit of the length (w) and the corresponding range for the first angle ($\alpha$) can be a function of the other values. In some configurations, however, the first angle ($\alpha$) can be between 50° and 70°. In some configurations, the first angle ($\alpha$) can exceed 60° such that condensate is more likely to be contained within the conduit 106 rather than flowing back into the humidification chamber 134.

With reference now to FIG. 13(b), the height (h) of the illustrated raised portion 160 is 4 mm. The length (w) of the raised portion 160 is 25 mm. The first angle ($\alpha$) of the raised portion 160 is 15 degrees and the second angle ($\theta$) is 35 degrees. The illustrated raised portion 160 creates a volume reduction of 4%.

With reference now to FIG. 13(c), the height (h) of the illustrated raised portion 160 is 6 mm. The length (w) of the raised portion 160 is 35 mm. The first angle ($\alpha$) of the raised portion 160 is 15 degrees and the second angle ($\theta$) is 60 degrees. The illustrated raised portion 160 creates a volume reduction of 14%.

With reference now to FIG. 13(d), the height (h) of the illustrated raised portion 160 is 6 mm. The length (w) of the raised portion 160 is 18 mm. The first angle ($\alpha$) of the raised portion 160 is 60 degrees and the second angle ($\theta$) is 60 degrees. The illustrated raised portion 160 creates a volume reduction of 8%.

FIGS. 14(a)-14(d) correspond to FIGS. 13(a)-13(d) and demonstrate the effect on the flow velocity in each configuration. FIGS. 14(a)-14(d) are flow velocity contours at a flow rate of 5 LPM. The contours of the no raised portion configuration of FIG. 14(a) clearly show that the elbow portion 162 creates an area of lower velocity gases, and it is in this area that the gases can cool. Each of the raised portions 160 of FIGS. 14(b)-14(d) has a positive effect on flow velocity, especially on velocities in the middle of the range. In addition, it can be seen that the more smoothly tapering asymmetric raised portions 160 of FIGS. 14(b) and 14(c) have significantly improved flow characteristics, because the shallow angle ($\alpha$) of the tapering end of the raised portion 160 reduces the area of potential dead space downstream of the raised portion 160.

FIGS. 15(a)-15(d) correspond to FIGS. 13(a)-13(d) and show reverse flow vectors extending from the planes of several cross sections downstream of the elbow portion 162. These vectors are overlaid onto the flow velocity contours of FIGS. 14(a)-14(d). The vector lengths represent the magnitudes of negative flow velocity components (i.e., the velocities of flow in the reverse direction to normal flow), which are indicative of recirculation that results in cooling gases. From these illustrations, it is apparent that the regions having the reverse flow components also have the lowest velocities, so it stands to reason that reducing recirculation will improve overall flow velocity and decrease cooling of the gases. Each of the raised portions 160 reduces recirculation relative to the configuration with no raised portion. The large asymmetric raised portion 160 of FIG. 15(c) appears to reduce recirculation the most. Again, the symmetric raised portion 160 of FIG. 15(d) does not appear to improve flow characteristics as much as the asymmetric raised portions 160 of FIGS. 15(b) and 15(c).

Figure 16A:
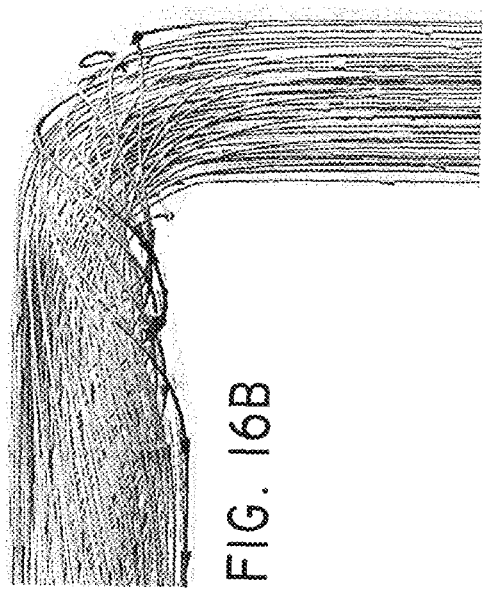
FIGS. 16(a)-16(c) illustrate show streamlines coloured by velocity magnitude and indicating paths taken by a zero mass particle if that particle were traveling with the flow.
Figure 16B:
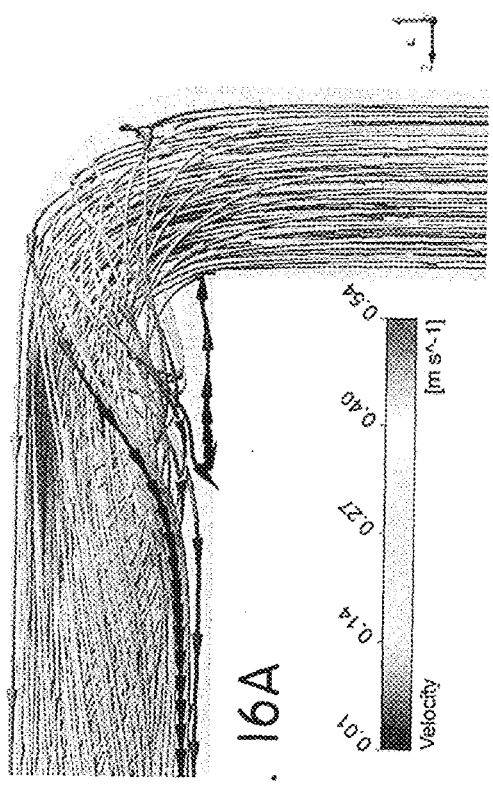
Figure 16C:
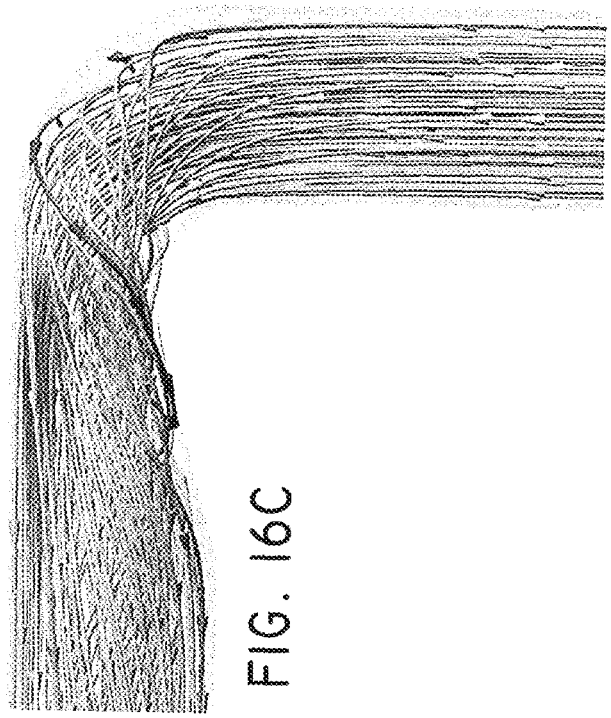

FIGS. 16(a)-16(c) correspond to FIGS. 13(a)-13(c); there is no corresponding illustration for FIG. 13(d). FIGS. 16(a)-16(c) show streamlines coloured by velocity magnitude and indicating paths taken by a zero mass particle if that particle were traveling with the flow. As shown in these illustrations, the recirculation and low velocity zones are greater in size following the sharp corner 170 of the elbow portion 162 where there is no raised portion. In addition, the larger raised portion 160 of FIG. 16(c) appears to improve performance over the smaller raised portion 160 of FIG. 16(b).

Figure 17:
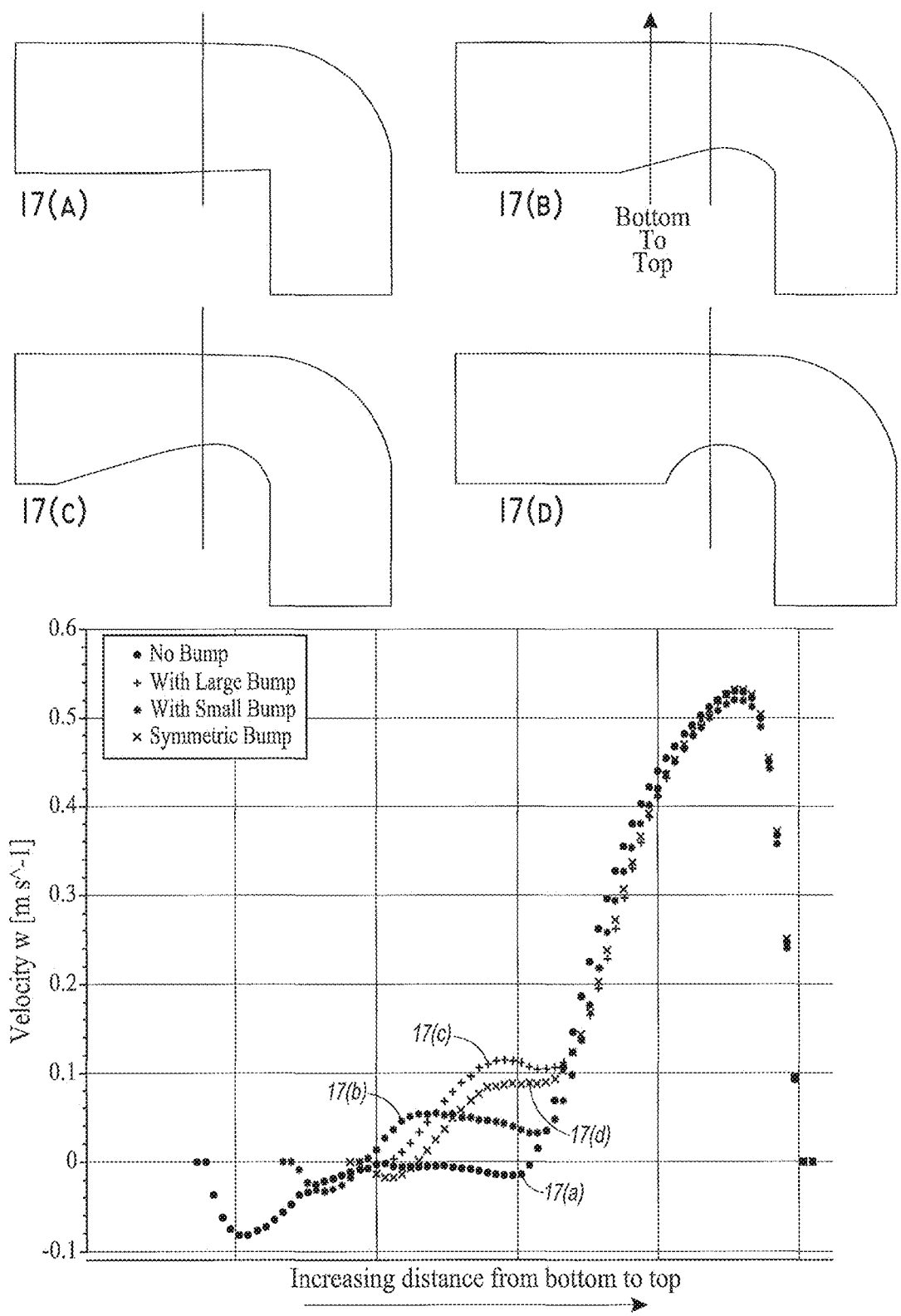
FIG. 17 is a plot illustrating the flow velocity components in a 5 LPM flow relative to the direction of flow at the same cross section for each of the configurations of FIGS. 13(a)-13(d).

FIG. 17 is a plot illustrating the flow velocity components in a 5 LPM flow relative to the direction of flow at the same cross section for each of the configurations of FIGS. 13(a)-13(d). Negative velocities indicate flow velocity components in the reverse direction compared to normal flow (i.e., recirculation). Each of the configurations demonstrates very similar velocities in the upper region of the cross-section (i.e., the right side of the plot) but there are significant differences in the lower region of the cross-section (i.e., the left side of the plot). The configuration of FIG. 13(a), which has no raised portion, demonstrates large regions of stagnation (near 0) and recirculation (below 0) before reaching the upper region and middle region, where positive flow is taking place. As shown, the larger raised portion 160 of FIG. 13(c) demonstrates the most improvement to reducing or eliminating recirculation and/or stagnant flow.

FIG. 18 is a plot comparing pressure magnitudes taken along a horizontal line that extends along an axis of the configurations of FIGS. 13(a)-13(d). As shown in the plot of FIG. 18, the pressure drop, and therefore the resistance to flow, remains very similar for all four of the designs of FIGS. 13(a)-13(d). As such, the benefits of recirculation reduction can be obtained without significantly impacting resistance to flow.

Figure 19B:
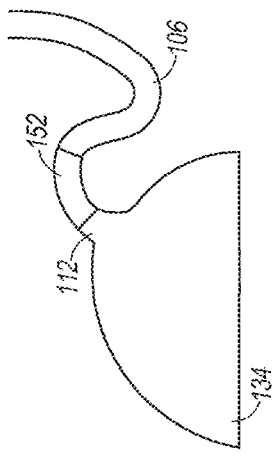
FIGS. 19(a)-19(d) show additional humidification chamber embodiments designed to impede condensate flowing back into the humidification chamber.
Figure 19D:
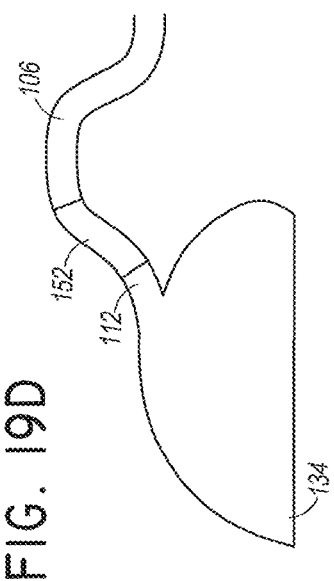
Figure 19A:
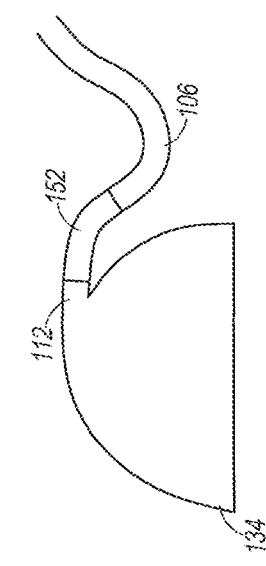
Figure 19C:
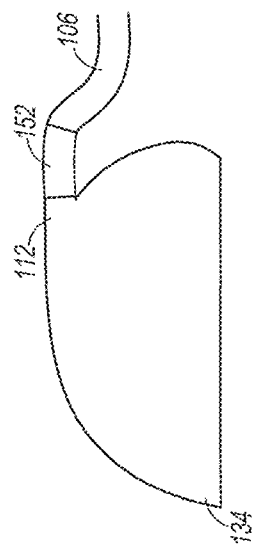

In addition to improving flow characteristics, the raised portions 160 provide the advantage of thwarting the flow of condensate back into the chamber 134. In configurations desiring to take advantage of this characteristic, the symmetrical raised portion 160 of FIG. 13(d) provides enhanced performance over the asymmetrical raised portions 160 of FIGS. 13(b) and 13(c). In addition, configurations as shown in FIGS. 19(a)-19(d) use different geometries to allow gravity to reduce the likelihood of condensate flowing back to the humidification chamber 134. In each of the embodiments in FIGS. 19(a)-19(c), either the conduit 106 or the connector 152 has a lower region before attaching to the port 112 of the humidification chamber 134. These regions may not inhibit gas flow, but these regions may allow pooling of any condensate formed while reducing the likelihood of the condensate flowing back to the humidification chamber 134. FIG. 19(d) uses an inverted form of the previous embodiments, where a high region is located proximally with a lower more distal region following, to reduce the likelihood of any condensate from flowing back to the humidification chamber 134.

These embodiments may provide solutions for condensate formation and pooling that may occur as a result of using a horizontal connection mechanism between a humidification chamber and a conduit. It is recognised that other mechanisms to reduce the likelihood of condensate flowing back to the humidification chamber may be possible and are not excluded from the scope of the disclosed apparatus and systems.

Unless the context clearly requires otherwise, throughout the description and the claims, the words "comprise". "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Where a value is used with a term of approximation, that number is intended to include the range of roundable values unless otherwise apparent from the context of use.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the present disclosure is intended to be defined only by the claims that follow.

What is claimed is:

1. A respiratory humidification system comprising:
   a humidification chamber that comprises:
   an outlet port defining at least a portion of a gases flow path, the outlet port comprising a vertical section, a horizontal section configured to engage with a connector of a conduit, and an elbow defining a corner at a transition between the vertical section and the horizontal section, the outlet port further comprises an opening configured to receive a probe; and
   an inlet port defining at least a second portion of the gases flow path; and
   a raised portion configured to reduce stagnant flow within the gases flow path, wherein the raised portion is positioned within of the outlet port or within an inspiratory circuit downstream of the outlet port.

2. The respiratory humidification system of claim 1, wherein the raised portion fills or at least partially fills a dead space region in the gases flow path in use.

3. The respiratory humidification system of claim 1, further comprising the conduit comprising the connector configured to engage the horizontal section of the outlet port.

4. The respiratory humidification system of claim 3, wherein the raised portion is integrally formed with the connector.

5. The respiratory humidification system of claim 3, wherein the raised portion is attached to the connector.

6. The respiratory humidification system of claim 3, wherein the raised portion is positioned in the conduit.

7. A respiratory humidification system comprising:
   a humidification chamber that comprises:
   an outlet port defining at least a portion of a gases flow path, the outlet port comprising a vertical section, a horizontal section configured to engage with a connector of a conduit, and an elbow defining a corner at a transition between the vertical section and the horizontal section, the outlet port further comprises an opening configured to receive a probe; and
   an inlet port defining at least a second portion of the gases flow path; and
   a raised portion configured to reduce an amount of condensate that is generated within the gases flow path in use, wherein the raised portion inhibits liquid flowing from the conduit to the humidification chamber in use.

8. The respiratory humidification system of claim 7, wherein the raised portion is asymmetrical along a length of the raised portion.

9. The respiratory humidification system of claim 7, wherein the raised portion is symmetrical along a length of the raised portion.

10. The respiratory humidification system of claim 7, wherein the raised portion forms a portion of the outlet port.

11. The respiratory humidification system of claim 7 further comprising the conduit comprising the connector configured to engage the horizontal section of the outlet port.

12. The respiratory humidification system of claim 11, wherein the raised portion forms a portion of the connector.

13. The respiratory humidification system of claim 11, wherein the raised portion forms a portion of the conduit.

14. A respiratory humidification system comprising:
    a humidification chamber that comprises:
    an outlet port defining at least a portion of a gases flow path, the outlet port comprising a vertical section, a horizontal section configured to engage with a connector of a conduit, and an elbow defining a corner at a transition between the vertical section and the horizontal section, the outlet port further comprises an opening configured to receive a probe; and
    an inlet port defining at least a second portion of the gases flow path;
    a raised portion configured to reduce recirculation of gases within the outlet port.

15. The respiratory humidification system of claim 14, wherein the raised portion is configured to reduce regions of low temperature along the gases flow path.

16. The respiratory humidification system of claim 15, wherein the raised portion is configured to reduce an amount of condensate that is generated within the regions of low temperature along the gases flow path in use.

17. The respiratory humidification system of claim 14, wherein the raised portion is located at or near the corner.

18. The respiratory humidification system of claim 14, wherein the raised portion is located within a region of the gases flow path that would be a recirculation region without the raised portion present.

* * * * *